(12) United States Patent
Zhang et al.

(10) Patent No.: US 11,718,671 B2
(45) Date of Patent: Aug. 8, 2023

(54) BISPECIFIC ANTIBODY AND USES THEREOF

(71) Applicant: EXCELMAB INC., Guangzhou (CN)

(72) Inventors: Wenjun Zhang, Guangzhou (CN); Cuijuan Chen, Guangzhou (CN); Xuemei Wei, Guangzhou (CN); Tonghui Luo, Guangzhou (CN)

(73) Assignee: Excelmab, Inc., Guangdong (CN)

( * ) Notice: Subject to any disclaimer, the term of this patent is extended or adjusted under 35 U.S.C. 154(b) by 397 days.

(21) Appl. No.: 16/965,541

(22) PCT Filed: Jan. 7, 2019

(86) PCT No.: PCT/CN2019/070655
§ 371 (c)(1),
(2) Date: Jul. 28, 2020

(87) PCT Pub. No.: WO2019/184549
PCT Pub. Date: Oct. 3, 2019

(65) Prior Publication Data
US 2021/0122823 A1    Apr. 29, 2021

(30) Foreign Application Priority Data

Mar. 27, 2018    (CN) .......................... 201810263832.0

(51) Int. Cl.
*C07K 16/28* (2006.01)
*C07K 16/32* (2006.01)
*A61K 39/00* (2006.01)

(52) U.S. Cl.
CPC .......... *C07K 16/2809* (2013.01); *C07K 16/32* (2013.01); *A61K 2039/505* (2013.01); *C07K 2317/31* (2013.01); *C07K 2317/51* (2013.01); *C07K 2317/515* (2013.01); *C07K 2317/522* (2013.01); *C07K 2317/524* (2013.01);
(Continued)

(58) Field of Classification Search
CPC ............................ C07K 16/2809; C07K 16/32
See application file for complete search history.

(56) References Cited

U.S. PATENT DOCUMENTS 8,236,308 B2    8/2012  Kischel et al.
9,493,563 B2    11/2016 Blein et al.
(Continued)

FOREIGN PATENT DOCUMENTS

CN    104558192 A    4/2015
CN    104829728       8/2015
(Continued)

OTHER PUBLICATIONS

Nordstrom, Breast Cancer Research, 2011, 1-14 (Year: 2011).*
(Continued)

*Primary Examiner* — Joanne Hama
*Assistant Examiner* — Adam Yamasaki Ring
(74) *Attorney, Agent, or Firm* — Hogan Lovells US LLP

(57) ABSTRACT

Provided is a novel antibody and a method for treating breast cancer. More specifically, the present disclosure relates to a bispecific antibody targeting CD3 and a tumor antigen target such as HER2, a preparation method, and uses thereof. The present disclosure also relates to a composition containing said antibody and a method for treating cancer by using the antibody.

16 Claims, 9 Drawing Sheets

Specification includes a Sequence Listing.

(52) U.S. Cl.
CPC ...... *C07K 2317/53* (2013.01); *C07K 2317/56* (2013.01); *C07K 2317/622* (2013.01); *C07K 2317/732* (2013.01); *C07K 2317/94* (2013.01)

(56) References Cited

U.S. PATENT DOCUMENTS

| | | | | |
|---|---|---|---|---|
| 2008/0260738 | A1* | 10/2008 | Moore | A61P 37/00 424/134.1 |
| 2012/0251531 | A1 | 10/2012 | Baehner et al. | |

FOREIGN PATENT DOCUMENTS

| | | |
|---|---|---|
| CN | 106062206 A | 10/2016 |
| CN | 107106682 A | 8/2017 |
| CN | 107108738 A | 8/2017 |
| CN | 107325182 A | 11/2017 |
| JP | 2014-514287 A | 6/2014 |
| JP | 2014-517844 A | 7/2014 |
| KR | 10-2015-015615 A | 2/2015 |
| WO | 2009/055074 A2 | 4/2009 |
| WO | 2012/162067 A2 | 11/2012 |
| WO | 2015/016608 A1 | 2/2015 |

OTHER PUBLICATIONS

Peng, Chemistry and Biology, 2015, 1134-1143 (Year: 2015).*
Ahmad, Clinical and Developmental Immunology, 2012, 1-15 (Year: 2012).*
Irani, Molecular Immunology, 2015, 171-182 (Year: 2015).*
Zhang, English translation via Espacenet of CN 104829728 A, 2015, 1-41 (Year: 2015).*
Teufl, ACS Synthetic Biology, 2022, 22, 1030-1039 (Year: 2022).*
International Search Report and Written Opinion issued in International Application No. PCT/CN2019/070655 dated Apr. 1, 2019.
Wuellner et al., "Bispecific CD3/HER2 Targeting FynomAb Induces Redirected T Cell-Mediated Cytolysis with High Potency and Enhanced Tumor Selectivity", Antibodies 2015, 4, 426-440, doi: 10.3390/antib4040426, published 2015, ISSN 2073-4468, www.mdpi.com/journal/antibodies, 15 total pages.
Decision to Grant issued in corresponding Japanese Application No. 2020-540284 dated Mar. 17, 2022, with English Translation, 3 total pages.
Notification to Grant Patent Right issued in corresponding Chinese Application No. 201810263832.0, date unknown, with English Translation, 4 total pages.
Notice of Acceptance issued in corresponding Australian Application No. 2019240974 dated Nov. 18, 2022, 3 total pages.
Examination Report issued in corresponding Australian Application No. 2019240974 dated May 23, 2022, 5 total pages.
Examination Report issued in corresponding Australian Application No. 2019240974 dated Aug. 3, 2022, 3 total pages.
Office Action issued in corresponding Canadian Application No. 3,089,254 dated Jun. 17, 2021, 4 total pages.
Office Action issued in corresponding Canadian Application No. 3,089,254 dated May 10, 2022, 4 total pages.
Office Action issued in corresponding European Application No. 19 776 671.0 dated Jul. 20, 2021, 6 total pages.
Notice of Reasons for Refusal issued in corresponding Japanese Application No. 2020-540284 dated Jul. 12, 2021, with English Translation, 10 total pages.
Notice of Reasons for Refusal issued in corresponding Japanese Application No. 2020-540284 dated Dec. 15, 2021, with English Translation, 4 total pages.
Office Action issued in corresponding Chinese Application No. 201810263832.0, date unknown, with English Translation, 4 total pages.
Search Report issued in corresponding Chinese Application No. 201810263832.0, date unknown, 3 total pages.
English Translation of Written Opinion issued in corresponding PCT Application No. PCT/CN2019/070655 dated Apr. 1, 2019, 5 total pages.

* cited by examiner

BISPECIFIC ANTIBODY AND USES THEREOF

CROSS-REFERENCE TO RELATED APPLICATIONS

This application is a U.S. National Stage application under 35 U.S.C. 371 of PCT/CN2019/070655, having an international filing date of Jan. 7, 2019, which designated the United States, which PCT application claims the benefit of Chinese Application No. 201810263832.0 filed on Mar. 27, 2018, each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Feb. 9, 2023, is entitled 046231_000045_SL.txt and is 60,123 bytes in size.

TECHNICAL FIELD

The present disclosure generally relates to an antibody and a method for treating cancer. Specifically, the present disclosure relates to a bispecific antibody targeting CD3 and tumor antigen targets such as HER2, a method for preparing the antibody and uses thereof. The present disclosure further relates to a composition comprising the above antibody and a method for treating cancer by using the antibody.

BACKGROUND

At present, the worldwide morbidity and mortality of malignant tumors are increasing year by year, and patients suffering from malignant tumors also become younger and younger. Although there are many anti-tumor drugs on the market, it is not only difficult to cure tumors through these drugs, but these drugs also have many side effects, which seriously affect the prognosis and the quality of life of patients. Therefore, the development of anti-tumor drugs that have a strong specific killing effect on tumor cells and few influences on normal cells has become a hot spot for the development of next-generation new drugs.

Anti-tumor drugs are divided into chemical drugs and biological drugs, wherein the former include alkylating agents, anti-metabolites and the like, while biological drugs include monoclonal antibodies, antibody-conjugated drugs, bispecific antibodies and the like. Herein, bispecific antibodies are artificially designed antibodies, which are composed of two components having different antigen binding sites, and can simultaneously bind to the two different antigen binding sites; and because of this special function thereof, it has a broad application prospect in immunotherapy of tumors.

SUMMARY

In an aspect, the present disclosure relates to an antibody or antibody fragment, comprising an antigen binding domain that binds to CD3, wherein the antigen binding domain that binds to CD3 has a heavy chain variable domain (VH) sequence of GXP2 (SEQ ID NO: 21) and a light chain variable domain (VL) sequence of GXP2 (SEQ ID NO: 22).

In some embodiments, the antibody or antibody fragment comprises a heavy chain sequence shown by SEQ ID NO: 9 and a light chain sequence shown by SEQ ID NO: 11.

In some embodiments, the antibody is a bispecific antibody or a multi-specific antibody.

In some embodiments, the antibody or antibody fragment further comprises another antigen binding domain aimed at antigen targets of tumor. In some embodiments, the antigen target of tumor is HER2.

In some embodiments, the antibody or antibody fragment comprises a heavy chain sequence selected from Her2-OB1 (SEQ ID NO: 1), Her2-OB2 (SEQ ID NO: 3), Her2-OB3 (SEQ ID NO: 5) and Her2-OB4 (SEQ ID NO: 7), and preferably, the antibody or antibody fragment comprises a heavy chain sequence of Her2-OB4 (SEQ ID NO: 7).

In some embodiments, the antibody fragment is selected from an Fab fragment, an Fab' fragment, an Fd fragment, an Fd' fragment, an Fv fragment, a dAb fragment, an F(ab')2 fragment, and a scFv fragment.

In an aspect, the present disclosure relates to a bispecific antibody having two heavy chains and one light chain, wherein a first heavy chain has scFv-hinge region-Fc from the N-terminus to the C-terminus; a second heavy chain has VH-CH1-hinge region-Fc from the N-terminus to the C-terminus; and the light chain has VL-CL from the N-terminus to the C-terminus, wherein the antigen binding domain of scFv of the first heavy chain binds to antigen target of tumor, and VH-CH1 of the second heavy chain and VL-CL of the light chain form another antigen binding domain, which binds to signal channel receptor on the surface of immune effector cells.

In some embodiments of the above-mentioned bispecific antibody, the antigen target of tumor is HER2, and the signal channel receptor is CD3.

In some embodiments of the above-mentioned bispecific antibody, VH of the second heavy chain has the sequence of SEQ ID NO: 21, and VL of the light chain has the sequence of SEQ ID NO: 22.

In some embodiments of the above-mentioned bispecific antibody, the second heavy chain has the sequence of GXP2-VH-OA (SEQ ID NO: 9), and the light chain has the sequence of GXP2-VL (SEQ ID NO: 11).

In some embodiments of the above-mentioned bispecific antibody, scFv of the first heavy chain has VH region of Ch4D5 monoclonal antibody, connecting peptide [(GGGGS)×N, N=3 (SEQ ID NO: 23), 4 (SEQ ID NO: 31), 5 (SEQ ID NO: 32)] and VL region of Ch4D5 monoclonal antibody from the N-terminus to the C-terminus; or has VL region of Ch4D5 monoclonal antibody, connecting peptide [(GGGGS)×N, N=3 (SEQ ID NO: 23), 4 (SEQ ID NO: 31), 5 (SEQ ID NO: 32)] and VH region of Ch4D5 monoclonal antibody from the N-terminus to the C-terminus.

In some embodiments of the above-mentioned bispecific antibody, the first heavy chain has a sequence selected from the following group: Her2-OB1 (SEQ ID NO: 1), Her2-OB2 (SEQ ID NO: 3), Her2-OB3 (SEQ ID NO: 5), and Her2-OB4 (SEQ ID NO: 7), wherein the first heavy chain preferably has the sequence of Her2-OB4 (SEQ ID NO: 7).

In any embodiment of the above-mentioned bispecific antibody, CH2 of the second heavy chain may contain L234A and L235A mutations. In some embodiments, CH2 of the first heavy chain may contain L234A and L235A mutations.

In any embodiment of the above-mentioned bispecific antibody, CH3 of the second heavy chain may contain T394D, P395D, and P396D mutations, and CH3 of the first heavy chain may contain P395K, P396K, and V397K mutations; or CH3 of the second heavy chain may contain P395K, P396K, and V397K mutations, and CH3 of the first heavy chain may contain T394D, P395D, and P396D mutations.

In some embodiments, compared with wild-type Fc region of corresponding antibody, the binding of the chimeric Fc region composed of the first heavy chain and the second heavy chain of the bispecific antibody according to the present disclosure to an Fc receptor is reduced.

In some embodiments, compared with a murine monoclonal antibody, the bispecific antibody according to the present disclosure binds to CD3 molecules with an increased thermal denaturation temperature. In some embodiments, the increase in the thermal denaturation temperature thereof for binding to CD3 molecules is manifested by an increase in $\Delta T$ of at least 5° C. In some embodiments, the increase in the thermal denaturation temperature thereof for binding to CD3 molecules is manifested by an increase in $\Delta T$ of at least 10° C. In some embodiments, the increase in the thermal denaturation temperature thereof for binding to CD3 molecules is manifested by an increase in $\Delta T$ of at least 12° C. In some embodiments, the increase in the thermal denaturation temperature thereof for binding to CD3 molecules is manifested by an increase in $\Delta T$ of 5-15° C. In some embodiments, the increase in the thermal denaturation temperature thereof for binding to CD3 molecules is manifested by an increase in $\Delta T$ of 10-15° C.

In some embodiments, the bispecific antibody according to the present disclosure has tumor killing activity. In some embodiments, the tumor is a HER2-positive tumor. In some embodiments, the tumor is selected from tumors of breast cancer, gastric cancer, ovarian cancer, prostate cancer, and lung cancer. In some embodiments, the tumor killing activity is tested in an in vitro tumor killing test. In some embodiments, the tumor killing activity is tested in an in vivo tumor model in mice.

In any embodiment of the above-mentioned bispecific antibody, the first heavy chain, the second heavy chain, and/or the light chain are derived from IgG1, IgG2, IgG3, and IgG4. In some embodiments, the first heavy chain, the second heavy chain, and/or the light chain are derived from IgG1.

In another aspect, the present disclosure relates to a nucleic acid molecule, comprising a nucleotide sequence encoding the first heavy chain, the second heavy chain, and/or the light chain of the bispecific antibody according to the present disclosure.

In yet another aspect, the present disclosure relates to a vector containing a nucleic acid molecule according to the present disclosure.

In an aspect, the present disclosure relates to a host cell containing a nucleic acid molecule according to the present disclosure. In some embodiments, the host cell is selected from 293F cells and CHO cells.

In another aspect, the present disclosure relates to an antibody conjugate, comprising an antibody or antibody fragment, or a bispecific antibody according to the present disclosure; and a portion conjugated to the antibody or antibody fragment, or the bispecific antibody. In some embodiments, the conjugating portion may be selected from cytotoxins, radioisotopes, fluorescent labels, luminophores, chromogenic substances and enzymes.

In some embodiments, the portion conjugated to the antibody or antibody fragment, or the bispecific antibody according to the present disclosure for forming an antibody conjugate is a cytotoxin. In some embodiments, the cytotoxin is selected from colchicine, emtansine, maytansinoid, auristatin, vindesine, tubulysin and the like.

In some embodiments, the portion conjugated to the antibody or antibody fragment, or the bispecific antibody according to the present disclosure for forming an antibody conjugate is a radioisotope. In some embodiments, the radioisotope is selected from radioisotopes such as $At^{211}$, $I^{131}$, $I^{125}$, $Y^{90}$, $Re^{186}$, $Re^{188}$, $Sm^{153}$, $Bi^{212}$ and $P^{32}$.

In some embodiments, the portion conjugated to the antibody or antibody fragment, or the bispecific antibody according to the present disclosure for forming an antibody conjugate is selected from fluorescent labels, luminophores, and chromogenic substances, e.g. FITC, luciferase, HRP and the like.

In some embodiments, the portion conjugated to the antibody or antibody fragment, or the bispecific antibody according to the present disclosure for forming an antibody conjugate is an enzyme, for example, an enzyme-active toxin derived from bacteria, fungi, plants or animals, including active fragments and/or variants thereof.

In yet another aspect, the present disclosure relates to a pharmaceutical composition, comprising an antibody or antibody fragment, a bispecific antibody, or an antibody conjugate according to the present disclosure; and optionally a pharmaceutically acceptable vector, a surfactant, and/or a diluent.

In some embodiments, in addition to the antibody or antibody fragment, the bispecific antibody or the antibody conjugate according to the present disclosure, the pharmaceutical composition further comprises one or more additional therapeutic agents. In some embodiments, the additional therapeutic agent is selected from tumor immune drugs such as Opdivo, Keytruda, Tecentriq, Imfinzi, Yervoy and the like.

In an aspect, the present disclosure relates to the use of an antibody or antibody fragment, a bispecific antibody, an antibody conjugate, or a pharmaceutical composition according to the present disclosure in the preparation of a drug for treating disease. In some embodiments, the disease refers to cancers, preferably, a HER2-positive cancer.

In some embodiments, the cancer is selected from breast cancer, gastric cancer, ovarian cancer, prostate cancer, and lung cancer.

In another aspect, the present disclosure relates to the use of an antibody or antibody fragment, a bispecific antibody, an antibody conjugate, or a pharmaceutical composition according to the present disclosure for treating a HER2-positive cancer.

In yet another aspect, the present disclosure relates to a method for treating a disease, comprising a step of administering, to a subject, an antibody or antibody fragment, a bispecific antibody, an antibody conjugate, or a pharmaceutical composition according to the present disclosure.

In some embodiments, the disease refers to cancers, preferably, a HER2-positive cancer. In some embodiments, the cancer is selected from breast cancer, gastric cancer, ovarian cancer, prostate cancer, and lung cancer.

In an aspect, the present disclosure relates to a polypeptide, having an amino acid sequence of SEQ ID NO: 21. In another aspect, the present disclosure relates to a polypeptide, having an amino acid sequence of SEQ ID NO: 22.

In an aspect, the present disclosure relates to a polypeptide, having an amino acid sequence of SEQ ID NO: 9. In another aspect, the present disclosure relates to a polypeptide, having an amino acid sequence of SEQ ID NO: 11.

BRIEF DESCRIPTION OF THE DRAWINGS

FIG. 2A is a non-reducing SDS-PAGE electrophoretogram, and FIG. 2B is a reducing SDS-PAGE electrophoretogram. In the figures, M is the molecular weight marker of protein, and lanes 2-7 are bispecific antibody samples in different collection tubes.

FIG. 6A: a 37° C. incubator and non-reducing SDS-PAGE; FIG. 6B: a 37° C. incubator and reducing SDS-PAGE; FIG. 6C: a 40° C. incubator and non-reducing SDS-PAGE; and FIG. 6D: a 40° C. incubator and reducing SDS-PAGE.

FIG. 7A shows non-reducing and reducing SDS-PAGE results; FIG. 7B shows CD3 ELISA results; and FIG. 7C shows HER2 ELISA results.

FIG. 8A: donor #1, IL-6; FIG. 8B: donor #1, TNF-α; FIG. 8C: donor #2, IL-6; and FIG. 8D: donor #2, TNF-α.

FIG. 9A: the target cells are SKBR-3 cells; FIG. 9B: the target cells are NCI-N87 cells; FIG. 9C: the target cells are MCF-7 cells; and FIG. 9D: the target cells are 293F cells.

DETAILED DESCRIPTION OF THE DISCLOSURE

Terms and Abbreviations

Figure 1:
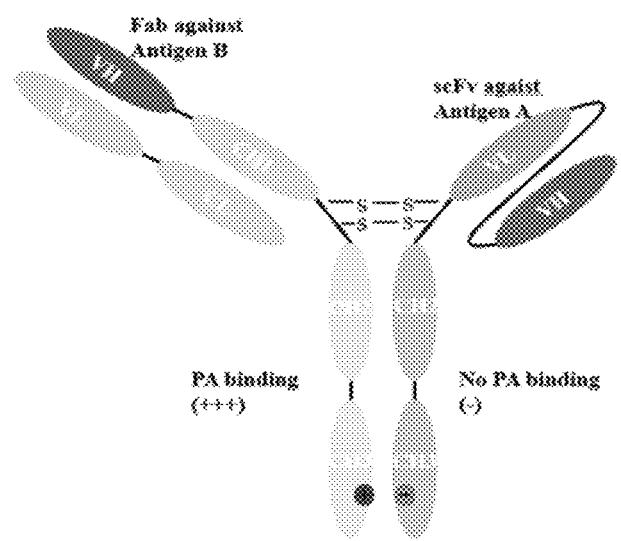
FIG. 1 shows a schematic diagram of the molecular structure of a bispecific antibody according to the present disclosure.

Unless otherwise defined herein, the scientific and technical terms and abbreviations thereof used in combination with the present disclosure shall have meanings that could be generally understood by a person ordinarily skilled in the art to which the present disclosure relates. Partial terms and abbreviations used in the context are enumerated in the following contents.

Ab: antibody;
Ig: immunoglobulin;
HC: heavy chain;
LC: light chain;
VH: heavy chain variable domain;
CH: heavy chain constant domain;
VL: light chain variable domain;
CL: light chain constant domain;
Fab: antigen binding fragment;
hinge region;
Fc region: fragment crystallizable region;
mAbs: monoclonal antibodies;
ADCC: antibody-dependent cell-mediated cytotoxicity;
CDC: complement dependent cytotoxicity;
NK cell: natural killing cell;
BsAb: bispecific antibody;
TCR: T cell receptor;
MHC: major histocompatibility complex;
CDR: complementarity determining region referring to antigen
complementary binding region of antibodies;
ITAM: immunoreceptor tyrosine-based activation motif;
HER2: human epidermal growth factor receptor-2;
scFv: single-chain variable fragment, also called as single-chain antibody;
ACI: adoptive cellular immunotherapy;
LAK cell: lymphokine-activated killer cell;
TIL cell: tumor infiltrating lymphocyte;
CIK cell: cytokine-induced killer cell;
CAR-T: chimeric antigen receptor T-cell immunotherapy.

Terms "polypeptide" and "protein" are interchangeable in the context, and refer to a polymer composed of amino acid residues. The carboxyl terminus of one amino acid and the amino terminus of another amino acid are connected to each other by forming a peptide bond through dehydration condensation. Polypeptide chains and proteins can be synthesized chemically or expressed recombinantly, and there is no restriction on the minimum amino acid length.

As used herein, the term "amino acid" refers to 20 naturally occurring amino acids or any unnatural amino acid analogues that may appear at a specific position.

As used herein, the term "amino acid mutation" refers to the addition, substitution, insertion, and/or deletion of a certain amino acid in a polypeptide chain.

As used herein, the term "antibody" includes full-length antibodies and antibody fragments, and relates to natural antibodies derived from organisms, genetically engineered antibodies, or antibodies obtained by recombinant technology. The term "antibody" includes monoclonal antibodies, polyclonal antibodies, bispecific antibodies, multi-specific antibodies and the like. The term "antibody" further includes murine antibodies, humanized antibodies, human antibodies and the like.

The term "antibody fragment" or "antigen binding fragment" includes, but is not limited to: (i) Fab fragments, which have $V_L$, $C_L$, $V_H$, and $C_H1$ domains; (ii) Fab' fragments, which are Fab fragments having one or more cysteine residues at the C-terminus of the $C_H1$ domain; (iii) Fd fragments with $V_H$ and $C_H1$ domains; (iv) Fd' fragments having $V_H$ and $C_H1$ domains and one or more cysteine residues at the C-terminus of the CH1 domain; (v) Fv fragments, which have $V_L$ and $V_H$ domains of a single arm of the antibody; (vi) dAb fragments, composed of VH domain or VL domain; (vii) F(ab')2 fragments, which is a divalent fragment comprising two Fab' fragments connected by a disulfide bridge at the hinge region; and (viii) a single-chain variable fragment (scFv). As used herein, the term "antibody fragment" not only includes the above-mentioned antibody fragments, but also includes antibodies modified from complete antibodies and new antibodies synthesized using recombinant DNA technology.

As used herein, the term "bispecific antibody" refers to an artificially designed antibody, which is composed of components of two different antigen binding sites and can simultaneously bind to two different antigen binding sites.

As used herein, "Fc" or "Fc region" or "Fc fragment" refers to a polypeptide consisting of CH2 and CH3 domains of IgA, IgD and IgG; or CH2, CH3, and CH4 domains of IgE and IgM, through a hinge region. Although the decomposition of the Fc fragment is variable, the heavy chain Fc fragment of human IgG usually refers to the polypeptide segment from A231 to its carboxy terminus.

As used herein, the term "hinge region" refers to a polypeptide chain in an antibody located between CH1 and CH2, which is rich in proline and is easy to stretch and bend. The recognized IgG hinge region is a polypeptide chain composed of amino acid residues form site 216 to site 230.

As used herein, the term "IgG" refers to a class of antibodies encoded by confirmed immunoglobulin γ genes, and human IgG includes IgG1, IgG2, IgG3, and IgG4.

As used herein, the term "EC50", i.e. concentration for 50% of maximal effect, refers to the corresponding antibody concentration evoking 50% of maximal effect.

As used herein, the term "humanized antibody" refers to an antibody or antibody fragment obtained after replacing partial or all CDR region of a human immunoglobulin (acceptor antibody) with CDR region of a non-human antibody (donor antibody), wherein the donor antibody may be a non-human antibody (e.g. derived from mice, rats, or rabbits) with an expected specificity, affinity or reactivity. In addition, some amino acid residues in the framework region (FR) of the acceptor antibody may also be replaced with corresponding amino acid residues of a non-human antibody, or with amino acid residues of other antibodies, so as to further improve or optimize one or more characteristics of the antibody.

As used herein, the term "epitope" or "antigenic determinant" refers to a site on an antigen that is specifically bound by immunoglobulins or antibodies. Most of the antigenic determinants exist on the surface of the antigenic substance, while some exist in the interior of the antigenic substance and are exposed only after being treated by enzymes or in other ways. An epitope or antigenic determinant is usually composed of chemically active surface groups of molecules, such as amino acids, carbohydrates or glycosyl side chains, and usually has specific three-dimensional structural characteristics and specific points and characteristics. The antigenic epitope may be "linear" or "conformational". In a linear epitope, all points of interaction between a protein and interacting molecules (such as antibodies) exist linearly along the primary amino acid sequence of the protein; and in a conformational epitope, the points of interaction exist across protein amino acid residues that are separated from each other. A natural antigenic substance may have various and multiple determinants. The larger the antigen molecules are, the greater the number of determinants is.

As used herein, the term "specific binding" refers to a non-random binding reaction between two molecules, such as the reaction between an antibody and the antigen it targets. In some embodiments, an antibody that specifically binds to a specific antigen (or an antibody that is specific for a specific antigen) means that the antibody binds to the antigen with an affinity (KO) less than about $10^{-5}$ M, for example, less than about $10^{-6}$ M, $10^{-7}$ M, $10^{-8}$ M, $10^{-9}$ M, or $10^{-10}$ M or with a much less affinity. In some embodiments of the present disclosure, the term "targeting" refers to specific binding.

As used herein, the term "$K_D$" refers to the dissociation equilibrium constant of a specific antibody-antigen interaction and is used to describe the binding affinity between an antibody and an antigen. The smaller the equilibrium dissociation constant is, the tighter the antibody-antigen binding and the higher the affinity between the antibody and the antigen will be. Generally, an antibody binds to an antigen with an equilibrium dissociation constant (KO) less than about $10^{-5}$ M, for example, less than about $10^{-6}$ M, $10^{-7}$ M, $10^{-8}$ M, $10^{-9}$ M, or $10^{-10}$ M, or with a much less equilibrium dissociation constant.

As used herein, the term "vector" refers to a nucleic acid vehicle into which a polynucleotide can be inserted. A vector is called as expression vector, when the vector enables the expression of the protein encoded by the inserted polynucleotide. The vector can be introduced into a host cell by way of e.g. transformation, transduction or transfection, and then enables the expression of the carried genetic material element in the host cell. Vectors would be recognized by a person skilled in the art and include, but are not limited to: (1) plasmids; (2) phagemids; (3) cosmids; (4) artificial chromosomes, such as yeast artificial chromosome (YAC), bacterial artificial chromosome (BAC) or artificial chromosome derived from P1 (PAC); (5) bacteriophages such as A bacteriophage or M13 bacteriophage; and (6) animal viruses such as retrovirus (including lentivirus), adenovirus, adeno-associated virus, herpesvirus (such as herpes simplex virus), poxvirus or baculovirus. A vector may contain multiple elements that control expression, including but not limited to, promoter sequences, transcription initiation sequences, enhancer sequences, selection elements, and reporter genes; in addition, the vector may further contain a replication origin.

Antibodies are immunoglobulins that are capable of specifically binding to antigens and are secreted by plasmocytes after that the antigens stimulate the organism to generate an immune response, and since they are naturally produced, they have fewer toxic and side effects. In the past decade, traditional monoclonal antibodies have achieved great success in tumor immunotherapy. By the end of 2016, 63 antibody-based drugs had been launched globally, and the global sales of antibodies in 2016 exceeded 100 billion US dollars. Of the top 10 drugs globally sold in 2016, 7 were biological drugs, 6 of which were antibody-based drugs, accounting for more than 20% of global drug sales. The mechanism of action of monoclonal antibody drugs includes blocking growth signals, blocking tumor angiogenesis, inducing apoptosis, and activating immune cells to produce immune effects, wherein monoclonal antibodies play important functions mainly by enhancing ADCC (antibody dependent cellular cytotoxicity) and ADCP (antibody dependent cellular phagocytosis) by way of activating cells through binding between Fc and FcγR (Fcγ-receptor) on the surface of immune cells (e.g. NK cells, monocytes and the like), or by enhancing CDC (complement dependent cytotoxicity) through the binding between Fc and the complement protein C1q, so as to achieve a cell killing effect.

The superiority of antibody drugs over traditional chemical therapeutic methods lies in the low toxicity and high specificity thereof, but antibody drugs still face the problem of low overall effectiveness. Furthermore, the therapeutic effect of antibody drugs is also plagued by drug resistance, and drug resistance would easily be caused by single target immunotherapy due to the tumor heterogeneity and the regulation of multiple signal pathways of the tumor cells themselves. These problems are related to the mechanism of action of monoclonal antibodies, which bind to Fc receptors on the surface of NK cells through their own Fc fragments, thereby activating NK cells to kill tumors. However, there is genetic polymorphism in human Fc receptors, and people who express high-affinity receptors (VV genotypes) account for only about 20%, while people who express low affinity have a poor response rate to the effects of monoclonal antibodies. These all determine that the overall response rate of monoclonal antibody drugs in the population is not high. Moreover, NK cells only account for about 5-8% of the total immune cell PBMC, and monoclonal antibody drugs cannot play the role of other immune cells during tumor killing.

At present, it is generally believed that T cells are the most important immune cells for anti-tumor killing, and account for more than 20% of the total PBMC, including CD8+ cytotoxic T cells, CD4+ helper T cells and the like. In order to establish specific anti-tumor cellular immunity in tumor patients' body, many bispecific antibodies that can simultaneously bind to tumor-associated antigens and receptors for T cell activation signaling pathways are designed. Such bispecific antibodies have one end for binding to acceptor molecules on T cells or other immune cells, such as CD3, TCR, CD28, CD16, NKG2D, while the other end can bind to targets on tumor cells, hereby promoting that immune T cells can recognize and bind to tumor cells, and forming an immune bridged chain to eliminate tumor cells.

The inventors conducted deep analysis and comparison of multiple murine antibodies against human CD3 complex, including CRIS-7, UCHT-1, TRX4, OKT3, MEM-57, SP34, HiT3a, and sequential optimization and humanized modification were performed for one of the murine antibody GXP (SP34).

GXP (SP34) is a murine monoclonal antibody against human CD3, and has been disclosed in many patent documents, and some companies have carried out humanized modification thereto (U.S. Pat. No. 9,587,021, PCT/US20121038219). The inventors performed humanized modification on framework region sequences of the VH and VL thereof and kept all the CDR1, CDR2 and CDR3 sequences of the murine heavy chain and light chain unchanged. Another important principle is to keep the murine sequence near the N-terminus or C-terminus of each CDR region as much as possible, so as to reduce the influence on the structural stability of the antibody and on the affinity for the antigen.

The final humanized sequence of the antibody determined by the inventors is named GXP2, and compared with the wild-type antibody, the humanized sequence GXP2 of the CD3 murine antibody optimized by the present disclosure has obtained many unique properties and advantages. These new characteristics make this new humanized antibody more suitable for the development of antibody drugs. Specifically, compared with the murine antibody or other humanized sequences, the antibody sequence optimized according to the present disclosure show significantly increased expression of the antibody protein, great improvement of the thermal stability, and improved affinity and binding to CD3 antigen, and show stronger tumor killing activity, when being applied to the preparation of a bispecific antibody. This humanized sequence disclosed in the present disclosure has more advantages and characteristics than humanized sequences from other companies, and shows better tumor killing activity when being applied to the preparation of a new anti-tumor drug; moreover, the physical and chemical stability thereof is also greatly improved, which indicates better suitableness for the screening and development of anti-tumor drugs; and this inventive achievement constitutes the beneficial effect and extremely high medical application value of the present disclosure.

Therefore, in an aspect, the present disclosure relates to an antibody or antibody fragment, comprising an antigen binding domain that binds to CD3, wherein the antigen binding domain that binds to CD3 has a heavy chain variable domain (VH) sequence of GXP2 (SEQ ID NO: 21) and a light chain variable domain (VL) sequence of GXP2 (SEQ ID NO: 22). In an embodiment, the antibody or antibody fragment may be a monoclonal antibody or an antigen binding fragment thereof. In another embodiment, the antibody or antibody fragment may be chimeric, CDR grafted, humanized, or fully human.

In some embodiments, the antibody or antibody fragment comprises a heavy chain sequence shown by SEQ ID NO: 9 and a light chain sequence shown by SEQ ID NO: 11.

In some embodiments, the antibody of the present disclosure is a bispecific antibody or a multi-specific antibody, which further comprises another antigen binding domain against antigen target of tumor. In some embodiments, the antigen target of tumor is human epidermal growth factor receptor-2 (HER2).

Many tumor-associated antigens associated with specific cancers have been identified. As used herein, the term "antigen target of tumor" refers to an antigen that is differentially expressed by cancer cells, and therefore can be utilized to target cancer cells. Cancer antigens are antigens that can potentially stimulate a significant tumor-specific immune response. Some of these antigens are encoded by normal cells, but not necessarily expressed by normal cells. These antigens can be characterized as those that are normally silent (i.e. not expressed) in normal cells, those that are expressed only at specific differentiative stages, and those that are expressed at specific times, such as embryonic and fetal antigens. Other cancer antigens are encoded by mutant cytogenes such as oncogenes (e.g. activated ras oncogenes), suppressor genes (e.g. mutant p53) and fusion proteins resulting from internal deletions or chromosome translocations. Other cancer antigens can be encoded by virogenes, such as genes carried on RNA and DNA tumor viruses. Many tumor antigens have been defined based on multiple solid tumors: MAGE 1, 2, and 3; and defined by immunity: MART-1/Melan-A, gp100, carcinoembryonic antigen (CEA), HER-2, mucin (i.e. MUC-1), prostate-specific antigen (PSA) and prostatic acid phosphatase (PAP). In addition, viral proteins such as hepatitis B (HBV), Epstein-Barr virus (EBV), and human papilloma virus (HPV) have been shown to respectively play important roles in the development of hepatocellular carcinoma, lymphoma, and cervical cancer. However, tumors use or benefit from a series of different immune evasion mechanisms, making the immune system of cancer patients often unable to recognize or respond to tumor antigens. Some examples of cancer antigens commonly associated with spermatocytes or spermatogonia of the testicle, the placenta and the ovary include cancer-testicle (CT) antigens BAGE, GAGE, MAGE-1 and MAGE-3, NY-ESO-1, SSX. These antigens are present in melanoma, lymphoma, lung cancer, bladder cancer, colon cancer, and breast cancer (e.g. as described in Butterfield et al., J. Immunotherapy 2008; 31: 294-309; and Markowicz et al., J Clin Oncol 27: 15s, 2009). Cancer antigens commonly found in melanocytes, epithelial tissues, prostate and colon further include differentiation antigens Gp100, Melan-A/Mart-1, tyrosinase, PSA, CEA and Mammaglobin-A. These antigens are present in melanoma, prostate cancer and colon cancer, and breast cancer. Some cancer antigens are shared antigens that are commonly expressed at low levels but overexpressed in cancers. Examples of overexpressed cancer antigens include p53, HER-2/neu, livin, and survivin found in esophagus, liver, pancreas, colon, breast, ovary, bladder, and prostate cancers. Other cancer antigens are unique, such as β-catenin-m, β-actin/4/m, myosin/m, HSP70-2/m, and HLA-A2-R170J that are related to one or more of melanoma, non-small cell lung cancer, and kidney cancer. Other cancer antigens are tumor-associated carbohydrate antigens commonly found in epithelial tissues such as renal, intestinal, and colorectal tissues. These cancer antigens include GM2, GD2, GD3, MUC-1, sTn, abd globo-H, which can be found in melanoma, neuroblastoma, colorectal cancer, lung cancer, breast cancer, ovarian cancer and prostate cancer. Additional tumor antigens and peptide epitopes thereof are described in U.S. Pat. Nos. 7,906,620; 7,910,692; 8,097,242; 7,935,531; 8,012,468; 8,097,256; 8,003,773; Tartour et al., Immunol Lett 2000; 74(1): 1-3, which is entirely incorporated herein by reference. In some embodiments, complete cancer antigens are used, while in other embodiments, peptide epitopes of cancer antigens (prepared by proteolytic digestion or recombinant) are used. Therefore, non-limiting examples of tumor or cancer antigens for use with the composition and method described herein include, but are not limited to Her2, prostate stem cell antigen (PSCA), PSMA (prostate-specific membrane antigen), β-catenin-m, B cell maturation antigen (BCMA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, Mammaglobin-A, melanoma-associated antigen (MAGE), CD34, CD45, CD99, CD117, chromogranin, cytokeratin, desmin, glial fibrillary acidic protein (GFAP), gross cystic disease fluid protein (GCDFP-15), EBV, gp100, HMB-45 antigen, protein melan-A (melanoma antigen recognized by T lymphocytes; MART-1), livin, survivin, myo-D1, muscle-specific actin (MSA), neurofilament, neuron-specific enolase (NSE), placental alkaline phosphatase, synaptic vesicle protein, thyroglobulin, thyroid transcription factor-1, pyruvate kinase isoenzyme M2-type dimer form (tumor M2-PK), CD19, CD22, CD27, CD30, CD70, GD2 (ganglioside G2) EphA2, CSPG4, CD138, FAP (fibroblast activation protein), CD171, kappa, lambda, 5T4, $\alpha_v\beta_6$ integrin, B7-H3, B7-H6, CAIX, CD19, CD20, CD22, CD30, CD33, CD44, CD44v6, CD44v7/8, CD70, CD123, EGFR, EGP2, EGP40, EpCAM, fetal AchR, FRa, GAGE, GD3, HLA-A1+MAGE1, MAGE-3, HLA-A1+NY-ESO-1, IL-11Rα, IL-13Ra2, Lewis-Y, Muc16, NCAM, NKG2D Ligands, NY-ESO-1, PRAME, ROR1, SSX, survivin, TAG72, TEMs, VEGFR2, EGFRvIII (epidermal growth factor variant III), sperm protein 17 (Sp17), mesothelin, PAP (prostatic acid phosphatase), prostein, TARP (T cell receptor γ alternate reading frame protein), Trp-p8, STEAP1 (six-transmembrane epithelial antigen of the prostate 1), HSP70-2/m and HLA-A2-R170J, tyrosinase, abnormal ras protein or abnormal p53 protein.

HER2 is a second member of the human epidermal growth factor receptor family (also known as the ErbB family). This family belongs to type I tyrosine kinase, which has four members: HER1, HER2, HER3, and HER4, plays a very important role in regulating the growth, the differentiation and the metastasis of normal or abnormal epidermal cells, and thus is closely related to the occurrence and development of multiple tumors.

HER2 is located on human chromosome 17q21 and encodes a transmembrane protein having a molecular weight of 185 KD and tyrosine kinase activity (Akiyama T et al., The product of the human c-erbB-2 gene: a185-kilodalton glycoprotein with tyrosine kinase activity, Science, 1986, Jun 27; 232 (4758): 1644-6). HER2 is usually expressed only in the fetal period, and is slightly expressed in few normal tissues after adulthood, such as mammary gland, gastrointestinal tract, kidney and heart (Olayioye Mass., Update on HER-2 as a target for cancer therapy: intracellular signaling pathways of ErbB2/HER-2 and family members, Breast Cancer Res. 2001; 3: 385-9; Yamamoto T et al., Similarity of protein encoded by the human c-erbB-2 gene to epidermal growth factor receptor, Nature, 1986; 319: 230-4). Under normal circumstances, the HER2 gene in cells is in an inactive state, and there are only 2 copies; when a gene mutation occurs, the HER2 gene can be activated and amplified 20-times or more, the transcription is then up-regulated and the protein synthesis is increased, which inhibits tumor cell apoptosis and promotes the proliferation of tumor cells; and also the tumor cell invasion can be enhanced by promoting the angiogenesis and the lymphangiogenesis of tumor tissues. In addition, after dimerization and autophosphorylation, HER2 protein can activate the PI3K/AKT pathway and the RAS/MAPK signaling pathway, so as to promote unlimited cell proliferation and differentiation, and also inhibit cell apoptosis, thereby promoting cell cancerization (Browne B C et al., HER-2 signaling and inhibition in breast cancer. Curr Cancer Drug Targets 2009; 9(3): 419-38; and Castaneda C A et al., The phosphatidyl inositol 3-kinase/AKT signaling pathway in breast cancer, Cancer Metastasis Rev 2010; 29(4): 751-9). In addition, the overexpression of HER2 can initiate a variety of metastasis-associated mechanisms, thereby increasing the migration ability of tumor cells, including cell migration rate, invasiveness and the like. In general, tumors exhibiting HER2 gene amplification and/or protein overexpression are usually highly malignant and have strong metastatic ability. It can be seen that the overexpression of the HER2 gene is not only closely related to the occurrence and development of tumors, but also an important clinical treatment monitoring and prognostic index, and is an important target selected by targeted therapeutic drugs for tumors (Slamon D J et al., Use of chemotherapy plus a monoclonal antibody against HER2 for metastatic breast cancer that overexpression HER2, N Engl J Med. 2001, Mar. 15; 344(11): 783-92).

The study found that HER2 overexpression exists in a variety of malignant tumors, including breast cancer, gastric cancer, ovarian cancer, prostate cancer, and lung cancer. 20%-30% of primary breast cancers have amplification and protein overexpression of HER2 gene, which are important factors that cause malignant metastasis of tumor cells. The condition of breast cancer patients with HER2 overexpression progresses rapidly, the chemotherapy remission period is short, the effect of endocrinotherapy is poor, and the disease-free survival and overall survival rate are low. Studies have shown that the survival rate of HER2-negative metastatic breast cancer patients is 17-22 months, while the survival rate of HER2 patients is only 8-10 months, only half of the former (Slamon D J et al., Science 1987; 235: 177-82).

The morbidity of gastric cancer ranks first among all kinds of malignant tumors in China, and HER2 is overexpressed in 7%-34% of gastric cancers. Gastric cancer has a poor prognosis, the overall survival rate of 5-year advanced gastric cancer is only 5%-20%, and the median survival time is not more than 1 year. Studies have shown that HER2 positive expression in gastric cancer is related to the tumor differentiation degree, Lauren classification, and WHO classification, and has no correlation with gender, age and tumor location.

HER2 is also overexpressed in 18%-43% of ovarian cancers (GlenMark communication). It has been reported in studies that compared with HER2-negative ovarian cancer patients (0/1+), the overall survival rate of HER2-positive patients (2+/3+) is significantly reduced (Verri E et al., HER2/neuoncopprotein overexpression in epthelial ovarian cancer: evaluation of its precalence and prognostic significance, Oncology, 2005, 68: 154-161).

In addition, HER2 is also overexpressed in prostate cancer and lung cancer. Signoretti et al. tested the DNA, RNA, and protein levels of prostate cancer samples at different clinical stages and found that the ratio of HER2 overexpression was different among patients receiving different treatment methods, wherein it accounts for 25% in patients that only underwent surgical resection of prostate cancer, and accounts for 59% in patients receiving anti-androgen therapy before surgery, while HER2 overexpression exists in up to 78% of patients that underwent failed androgen therapy and suffered from bone metastasis (androgen-dependent AI). The overexpression of HER2 in lung cancer is closely related to gene transcription and post-transcriptional modification.

HER2 targeted drugs currently used clinically include Trastuzumab (Herceptin®), Pertuzumab (Perjeta®), and Ado-trastuzumabemtansine (Kadcyla®) as mentioned above, which, although have achieved certain therapeutic effects, still have many limitations: (1) about 60-70% of patients had primary resistance to Herceptin; (2) about 70% of patients had acquired resistance after 1 year of treatment with Herceptin; and (3) the first-line therapeutic effect of Kadcyla is not as good as Herceptin, and its price is very high, causing a great financial burden on patients (GlenMark communication).

In the present disclosure, a ScFv structure binding to the tumor target Her2/neu is designed and constructed referring to the amino acid sequence of monoclonal antibody Ch4D5 (PDB Database #1N8E), and several forms are further designed, such as VH-linker-VL, VL-linker-VH, and VH-linker-VL plus L234A and L235A mutations. Specific designs are as follows:

In a first embodiment, the scFv that binds to the tumor target Her2 was formed by connecting, from the N-terminus to the C-terminus, VH of the anti-Her2 antibody Ch4D5 with an oligopeptide linker (GGGGS)×3 of 15 amino acids (SEQ ID NO: 23), and then with VL of Ch4D5. The obtained scFv is connected to the hinge region and the Fc having an OB mutation sequence (T394D, P395D, P396D), hereby forming a ScFv-Fc heavy chain that binds to Her2, namely Her2-OB1 (SEQ ID NO: 1).

In a second embodiment, the scFv that binds to the tumor target Her2 was formed by connecting, from the N-terminus to the C-terminus, VL of Ch4D5 with an oligopeptide linker (GGGGS)×3 of 15 amino acids (SEQ ID NO: 23), and then with VH of Ch4D5. The obtained scFv was connected to the hinge region and the Fc having an OB sequence, hereby forming a ScFv-Fc heavy chain that binds to Her2, namely Her2-OB2 (SEQ ID NO: 3).

In a third embodiment, the structure of the ScFv-Fc heavy chain that binds to the tumor target Her2 was similar to that in the first embodiment, that is, VH of the anti-Her2 antibody Ch4D5 was connected with an oligopeptide linker (GGGGS)×3 of 15 amino acids (SEQ ID NO: 23), and then connected with VL of Ch4D5. The obtained scFv was connected to the hinge region and the Fc having an OB sequence. Since NcoI and Bgl II multiple cloning sites are contained between the VL region and the hinge region of Her2-OB1 (SEQ ID NO: 1), an additional non-human amino acid TVAMVR (SEQ ID NO: 24) is contained. In this embodiment, this sequence was replaced with the human antibody sequence GEPK (SEQ ID NO: 25), hereby forming a ScFv-Fc heavy chain that binds to Her2, i.e. Her2-OB3 (SEQ ID NO: 5).

In a fourth embodiment, L234A and L235A mutations were introduced into the CH2 region of the heavy chain of the monoclonal antibody Ch4D5 on the basis of the third embodiment, so as to reduce the ADCC function and the CDC function of the antibody to avoid damages to T cells. The obtained sequence was Her2-OB4 (SEQ ID NO: 7).

The above four constructs all show high affinity for Her2/neu, wherein 0131, 0B3, and OB4 with a VH-linker-VL structure show higher affinity than 0B2 with a VL-linker-VH structure.

Therefore, in some embodiments, the antibody or antibody fragment of the present disclosure comprises a heavy chain sequence selected from Her2-OB1 (SEQ ID NO: 1), Her2-OB2 (SEQ ID NO: 3), Her2-OB3 (SEQ ID NO: 5) and Her2-OB4 (SEQ ID NO: 7), and preferably, the antibody comprises a heavy chain sequence of Her2-OB4 (SEQ ID NO: 7). The heavy chain sequence binds to HER2 with high affinity and forms a bispecific antibody or a multi-specific antibody with the VH sequence of GXP2 (SEQ ID NO: 21) and the VL sequence of GXP2 (SEQ ID NO: 22) (antigen binding domain that binds to CD3) as mentioned above, so as to treat HER2-positive cancers, such as HER2-positive breast cancer, gastric cancer, ovarian cancer, prostate cancer, and lung cancer.

In some embodiments, the antibody fragment as described above is selected from an Fab fragment, an Fab' fragment, an Fd fragment, an Fd' fragment, an Fv fragment, a dAb fragment, an F(ab')2 fragment, and a scFv fragment.

In an aspect, the present disclosure relates to a bispecific antibody, having two heavy chains and one light chain, wherein a first heavy chain has scFv-hinge region-Fc from the N-terminus to the C-terminus; a second heavy chain has VH-CH1-hinge region-Fc from the N-terminus to the C-terminus; and the light chain has VL-CL from the N-terminus to the C-terminus, wherein the antigen binding domain of scFv of the first heavy chain binds to an antigen target of tumor, and VH-CH1 of the second heavy chain and VL-CL of the light chain form another antigen binding domain, which binds to signal channel receptors on the surface of immune effector cells.

FIG. 1 shows a schematic diagram of the molecular structure of a bispecific antibody according to the present disclosure.

The bispecific antibody disclosed in the present disclosure has the following characteristics in structure:

1. The bispecific antibody molecule contains two different antigen binding fragments, one of them can specifically recognize tumor-associated antigens, and the other can specifically recognize and bind to signal pathway targets on immune effector cells. Thus, it can specifically capture immune cells in the human body, bring them to the vicinity of tumor cells, and can promote the formation of connecting bridges of immune effect between immune cells and tumor cells, thereby activating immune cells, such as T cells, NK cells, macrophages and the like, and killing and eliminating tumor cells.

2. Since one antigen binding fragment of the molecular structure has a scFv structure and the other antigen binding fragment has a Fab structure, the entire molecule is composed of two different heavy chains and one light chain, wherein the one light chain forming the Fab binding region can only bind to the heavy chain variable domain of this region, thus, there would be no mismatch between the light chain and the corresponding heavy chain.

3. Because the bispecific antibody molecule is of an asymmetric structure, a great amount of target product (heterodimer) and a small amount of non-target product (homodimer) produced during the production process are greatly different from each other in the molecular weight and the charge distribution, which is conducive to downstream purification and separation.

In some embodiments of the above-mentioned bispecific antibody, the antigen target of tumor is HER2, and the signal channel receptor is CD3. In some embodiments, VH of the second heavy chain has the VH sequence of GXP2 (SEQ ID NO: 21), and VL of the light chain has the VL sequence of GXP2 (SEQ ID NO: 22).

In some embodiments of the above-mentioned bispecific antibody, the second heavy chain has the sequence of GXP2-VH-OA (SEQ ID NO: 9), and the light chain has the sequence of GXP2-VL (SEQ ID NO: 11).

In some embodiments of the above-mentioned bispecific antibody, scFv of the first heavy chain has VH region of Ch4D5-monoclonal antibody, connecting peptide [(GGGGS)×N, N=3 (SEQ ID NO: 23), 4 (SEQ ID NO: 31), 5 (SEQ ID NO: 32)] and VL region of Ch4D5-monoclonal antibody from the N-terminus to the C-terminus; or has VL region of Ch4D5-monoclonal antibody, connecting peptide [(GGGGS)×N, N=3 (SEQ ID NO: 23), 4 (SEQ ID NO: 31), 5 (SEQ ID NO: 32)] and VH region of Ch4D5-monoclonal antibody from the N-terminus to the C-terminus.

In some embodiments of the above-mentioned bispecific antibody, the first heavy chain has a sequence selected from the following group: Her2-OB1 (SEQ ID NO: 1), Her2-OB2 (SEQ ID NO: 3), Her2-OB3 (SEQ ID NO: 5), and Her2-OB4 (SEQ ID NO: 7), wherein the first heavy chain preferably has the sequence of Her2-OB4 (SEQ ID NO: 7).

In any embodiment of the above-mentioned bispecific antibody, CH2 of the second heavy chain and/or CH2 of the first heavy chain may contain L234A and L235A mutations, so as to reduce the ADCC function and the CDC function of the antibody to avoid damages to T cells.

WO2017034770A1 discloses a method for transforming the heavy chain portion of an antibody to improve the binding activity and the specificity between two heavy chains, comprising: introducing following mutations into one heavy chain: P395K, P396K, and V397K, with the mutation being named as OA; and introducing following mutations into another heavy chain: T394D, P395D, and P396D, with the mutation being named as OB.

Thus, in any embodiment of the above-mentioned bispecific antibody, CH3 of the second heavy chain may contain P395K, P396K, and V397K mutations, and CH3 of the first heavy chain may contain T394D, P395D, and P396D mutations.

Alternatively, CH3 of the second heavy chain may contain T394D, P395D, and P396D mutations, and CH3 of the first heavy chain may contain P395K, P396K, and V397K mutations. The purpose is to enhance the binding affinity and the specificity between heavy chains.

In the description and claims, the residues in an immunoglobulin heavy chain is numbered in the way of EU index as described in Kabat et al., Sequences of Proteins of Immunological Interest, 5th Ed. Public Health Service, National Institutes of Health, Bethesda, Md. (1991), which is also available on the World Wide Web and is expressly and entirely incorporated herein by reference. "EU index as described in Kabat" refers to the residue numbering method of human IgG1 EU antibody. As used herein, the term "Kabat sequence numbering method" or "Kabat mark" refers to the sequence encoding the variable domain with the EU index numbering as described in Kabat. For the heavy chain variable domain, according to the Kabat numbering, the hypervariable domain ranges from amino acid sites 31 to 35 of CDR1, amino acid sites 50 to 65 of CDR2, and amino acid sites 95 to 102 of CDR3. For the light chain variable domain, according to the Kabat numbering, the hypervariable domain ranges from amino acid sites 24 to 34 of CDR1, amino acid sites 50 to 56 of CDR2, and amino acid sites 89 to 97 of CDR3.

In some embodiments, compared with wild-type Fc region of corresponding antibody, the binding of the chimeric Fc region composed of the first heavy chain and the second heavy chain of the bispecific antibody according to the present disclosure to an Fc receptor is reduced. For example, in some embodiments, its binding to an Fc receptor is reduced. Reduced binding to Fc receptor of the Fc region of the antibody can reduce the ADCC function and the CDC function of the antibody to avoid damages to T cells.

In some embodiments, compared with a murine monoclonal antibody, the bispecific antibody according to the present disclosure binds to CD3 molecules with an increased thermal denaturation temperature. For example, in some embodiments, the thermal denaturation temperature thereof for binding to CD3 molecules is increased. In some embodiments, the increase in the thermal denaturation temperature thereof for binding to CD3 molecules is manifested by an increase in $\Delta T$ of at least 5° C. In some embodiments, the increase in the thermal denaturation temperature thereof for binding to CD3 molecules is manifested by an increase in $\Delta T$ of at least 10° C. In some embodiments, the increase in the thermal denaturation temperature thereof for binding to CD3 molecules is manifested by an increase in $\Delta T$ of at least 12° C. In some embodiments, the increase in the thermal denaturation temperature thereof for binding to CD3 molecules is manifested by an increase in $\Delta T$ of 5-15° C. In some embodiments, the increase in the thermal denaturation temperature thereof for binding to CD3 molecules is manifested by an increase in $\Delta T$ of 10-15° C.

In some embodiments, the bispecific antibody according to the present disclosure has tumor killing activity. In some embodiments, the tumor is a HER2-positive tumor. In some embodiments, the tumor is selected from tumors of breast cancer, gastric cancer, ovarian cancer, prostate cancer, and lung cancer. In some embodiments, the tumor killing activity is tested in an in vitro tumor killing test. In some embodiments, the tumor killing activity is tested in an in vivo tumor model in mice.

In any embodiment of the above-mentioned bispecific antibody, the first heavy chain, the second heavy chain, and/or the light chain are derived from IgG1, IgG2, IgG3, and IgG4. In some embodiments, the first heavy chain, the second heavy chain, and/or the light chain are derived from IgG1.

In addition, in an aspect, the present disclosure relates to a polypeptide, having an amino acid sequence of SEQ ID NO: 21. In another aspect, the present disclosure relates to a polypeptide, having an amino acid sequence of SEQ ID NO: 22.

In an aspect, the present disclosure relates to a polypeptide, having an amino acid sequence of SEQ ID NO: 9. In another aspect, the present disclosure relates to a polypeptide, having an amino acid sequence of SEQ ID NO: 11.

Nucleic Acid, Vector, and Host Cell

In an aspect, the present disclosure relates to a nucleic acid, comprising a nucleotide sequence encoding the first heavy chain, the second heavy chain, and/or the light chain of the bispecific antibody according to the present disclosure.

In another aspect, the present disclosure relates to a vector comprising the nucleic acid according to the present disclosure, e.g. expression vector.

Examples of the expression vector according to the present disclosure include expression vectors constructed based on the pFUSEss CHIg-hG1 vector or other vectors. Herein, the anti-HER2 scFv domain is amplified by PCR, and restriction enzyme cutting sites (EcoR I and Xho I) are introduced into scFv; and the amplified gene fragment is connected with vector pFUSEss CHIg-hG1, which has undergone the restriction enzyme digestion, hereby obtaining an expression vector loaded with an anti-HER2 scFv-Fc, which is named as (pFuse HER2-OB).

Examples of the vector according to the present disclosure further include an expression vector loaded with an anti-CD3 heavy chain, named as (pFUSE GXP2-OA-VH), which is obtained by amplifying the VH fragment of the anti-CD3 heavy chain by PCR, introducing restriction enzyme cutting sites (EcoR I and Xho I) into the heavy chain, and then connecting to vector pFUSEss CHIg-hG1, which has undergone the restriction enzyme digestion.

Examples of the vector according to the present disclosure further include expression vectors constructed based on pcDNA 3.1(+) or other vectors. Herein, the VL fragment of the anti-CD3 light chain is amplified by PCR, restriction enzyme cutting sites (Hind III and Xho I) are introduced into the light chain, which is then connected with vector pcDNA 3.1(+), which has undergone the restriction enzyme digestion, hereby obtaining an expression vector with an inserted anti-CD3 light chain, which is named as (pCK GXP2-VL).

In an aspect, the present disclosure relates to a host cell comprising a nucleic acid molecule according to the present disclosure. In some embodiments, the host cell is selected from HEK293F cells and CHO cells.

The present disclosure further relates to a method for preparing a bispecific antibody, wherein the method comprises:

1. constructing a first heavy chain containing a binding region of scFv on a first expression vector, constructing a second heavy chain containing a binding region of Fab structure on a second expression vector, and constructing a light chain containing a binding region of Fab structure on a second vector or an optional third expression vector;

2. co-transfecting the host cells of a mammal with the first expression vector, the second expression vector, and the optional third expression vector together, wherein preferably, the cells are 293F cells or CHO cells;

3. culturing the transfected 293F cells or CHO cells and collecting the culture supernatant;

4. purifying the target bispecific antibody from the culture supernatant; wherein the separation step comprises: capturing antibody molecules with an Fc fragment in the expression supernatant with a protein A affinity chromatographic column, then realizing the separation of the target bispecific antibody from byproducts through cation-exchange chromatography, and finally concentrating and replacing the buffer solution.

In some embodiments, the first expression vector is pFuse HER2-OB. In some embodiments, the second expression vector is pFUSE GXP2-OA-VH. In some embodiments, the third expression vector is pCK GXP2-VL.

Antibody Conjugate

In recent years, antibody conjugates have received increasing attention due to their good targeting ability and anti-cancer activity. An antibody conjugate is composed of an antibody, a connecting short chain, and a conjugate selected from the following group: cytotoxins, radioisotopes, fluorescent labels, luminophores, chromogenic substances or enzymes, wherein the targeting ability of the antibody is combined with the above conjugate. After that the antibody conjugate enters the blood circulation, the antibody portion recognizes the target on the surface of the target cells; after recognizing the target, the antibody, through the target complex, enters the cells through the endocytosis of the cells, and then is gradually decomposed by the enzymes in the lysosome, then the toxic substance carried by the antibody is released into the cytoplasm and kills the target cells. Antibody conjugates can reduce the adverse reactions of chemical anti-tumor drugs and improve the selectivity of tumor treatment.

Accordingly, the present disclosure further relates to an antibody conjugate formed by the conjugation of the antibody or the bispecific antibody of the present disclosure with an additional portion. In some embodiments, the additional portion is selected from cytotoxins, radioisotopes, fluorescent labels, luminophores, chromogenic substances or enzymes.

In some embodiments, the portion conjugated to the antibody or the bispecific antibody according to the present disclosure for forming an antibody conjugate is a cytotoxin. In some embodiments, the cytotoxin refers to a substance inhibiting or preventing cell function and/or causing cytoclasis, and includes small molecule cytotoxins. In some embodiments, the cytotoxin is selected from colchicine, emtansine, maytansinoid, auristatin, vindesine, tubulysin and the like.

In some embodiments, the portion conjugated to the antibody or the bispecific antibody according to the present disclosure for forming an antibody conjugate is a radioisotope. In some embodiments, the radioisotope includes e.g. $At^{211}$, $I^{131}$, $I^{125}$, $Y^{90}$, $Re^{186}$, $Re^{188}$, $Sm^{153}$, $Bi^{212}$, $F^{32}$, and radioisotopes of Lu.

In some embodiments, the portion conjugated to the antibody or the bispecific antibody according to the present disclosure for forming an antibody conjugate is selected from fluorescent labels, luminophores, and chromogenic substances, e.g. FITC, luciferase, HRP and the like.

In some embodiments, the portion conjugated to the antibody or the bispecific antibody according to the present disclosure for forming an antibody conjugate is an enzyme, for example, an enzyme-active toxin derived from bacteria, fungi, plants or animals, including active fragments and/or variants thereof.

Pharmaceutical Composition and Method for Treating a Disease

In an aspect, the present disclosure relates to a pharmaceutical composition, comprising an antibody or antibody fragment, a bispecific antibody, or an antibody conjugate according to the present disclosure; and optionally a pharmaceutically acceptable vector, a surfactant, and/or a diluent.

The phrase "pharmaceutically acceptable vector" refers to a pharmaceutically acceptable material, composition or intermedium, such as a liquid or solid filler, a diluent, an excipient, a solvent, a medium, an encapsulating material, a manufacturing auxiliary (e.g. a lubricant, talc magnesium, calcium or zinc stearate or stearic acid) or a solvent encapsulating material, which are involved in maintaining the stability, solubility or activity of the LAP binder. Each vector must be "acceptable" in the sense of being compatible with the other ingredients of the formulation and not harmful to patients. Some examples of materials that can serve as pharmaceutically acceptable vectors include: (1) sugars, such as lactose, glucose and sucrose; (2) starches, such as corn starch and potato starch; (3) cellulose and derivatives thereof, such as sodium carboxymethyl cellulose, methyl cellulose, ethyl cellulose, microcrystalline cellulose, and cellulose acetate; (4) powdered tragacanth; (5) malt; (6) gelatin; (7) excipients, such as cocoa butter and suppository wax; (8) oils, such as peanut oil, cottonseed oil, safflower oil, sesame oil, olive oil, corn oil, and soybean oil; (9) glycols, such as propylene glycol; (10) polyols, such as glycerin, sorbitol, mannitol, and polyethylene glycol (PEG); (11) esters, such as ethyl oleate and ethyl laurate; (12) agar; (13) buffers, such as magnesium hydroxide and aluminum hydroxide; (14) alginic acid; (15) pyrogen-free water; (16) isotonic saline water; (17) Ringer's solution; (19) pH buffer solution; (20) polyester, polycarbonate and/or polyanhydride; (21) fillers, such as polypeptides and amino acids; (22) serum components, such as serum albumin, HDL, and LDL; (23) C2-C12 alcohols, such as ethanol; and (24) other non-toxic compatible substances used in pharmaceutical formulations. Releasing agents, coating agents, preservatives, and antioxidants can also be present in pharmaceutical formulations. Terms such as "excipient", "vector", "pharmaceutically acceptable vector" and the like are interchangeable in the context.

In some embodiments, in addition to the antibody, the bispecific antibody or the antibody conjugate according to the present disclosure, the pharmaceutical composition further comprises one or more additional therapeutic agents.

In some embodiments, the additional therapeutic agents include, but are not limited to, chemotherapeutic agents, growth inhibitors, cytotoxic agents, reagents for radiotherapy, anti-angiogenic agents, apoptotic agents, anti-tubulin agents, and other reagents for treating cancer, such as anti-CD20 antibodies, epidermal growth factor receptor (EGFR) antagonists (e.g. tyrosine kinase inhibitors), HER1/EGFR inhibitors (e.g. erlotinib (TARCEVA®), platelet-derived growth factor inhibitors (e.g. GLEEVEC™ (Imatinib Mesylate)), COX-2 inhibitors (e.g. celecoxib), interferons, cytokines, antagonists (e.g. neutralizing antibodies), which bind to one or more following target materials: PD-1, PD-L1, PD-L2 (e.g. pembrolizumab; nivolumab; MK-3475; AMP-224; MPDL3280A, MEDI0680; MSB0010718C, and/or MED14736; CTLA-4 (for example, tremelimumab (PFIZER) and ipilimumab); LAG-3 (for example, BMS-986016), CD103, TIM-3 and/or other TIM family members; CEACAM-1 and/or other CEACAM family members, ErbB2, ErbB3, ErbB4, PDGFR-β, BlyS, APRIL, BCMA or VEGF receptors, TRAIL/Apo2 and other bioactivators and organic chemical agents. A combination thereof is also specifically considered in the methods described herein.

In some embodiment, the additional therapeutic agent is a chemotherapeutic agent. Non-limiting examples of chemotherapeutic agents may include: alkylating agents, such as thiotepa and CYTOXAN® cyclophosphamide, temozolomide; alkyl sulfonates, such as busulfan, improsulfan, and piposulfan; aziridines, such as benzodepa, carboquone, meturedepa and uredepa; ethylenimines and methylamelamines, including altretamine, triethylenemelamine, trietylenephosphoramide (triethylenephosphoramide), triethiylenethiophosphoramide (triethylenethiophosphoramide), and trimethylolomelamine; acetogenin (especially bullatacin and bullatacinone); camptothecin (including synthetic analogue topotecan); bryostatin; callystatin; CC-1065 (including adozelesin, carzelesin and bizelesin synthetic analogues); cryptophycins (especially cryptophycins 1 and 8); dolastatin; duocarmycin (including synthetic analogues KW-2189 and CB1-TM1), eleutherobin; pancratistatin; sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas, such as carmustine, chlorozotocin, fotemustine, lomustine, nimustine and ranimustine; antibiotics, such as enediyne antibiotics (such as calicheamicin, especially calicheamicin γ1I and calicheamicin ω1I (see for example Agnew. Chem Intl. Ed. Engl., 33: 183-186 (1994)); anthracycline antibiotics (dynemicin), including dynemicin A; esperamicin; and neocarzinostatin chromophore and related chromoprotein enediyne antibiotic chromophores), aclacinomycin, actinomycin, anthramycin, azaserine, bleomycin, cactinomycin, carabicin, caminomycin (carminomycin), carzinophilin, chromomycinis (chromomycin), dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins, such as mitomycin C, mycophenolic acid, nogalamycin, olivomycin, peplomycin, porfiromycin (potfiromycin), puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogues, such as fludarabine, 6-mercaptopurine, thiamiprine, thioguanine; pyrimidine analogues, such as ancitabine, azacitidine, 6-azauridine, carmofur, cytarabine, dideoxyuridine, doxifluridine, enocitabine, floxuridine; androgens, such as calusterone, dromostanolone propionate, epitiostanol, mepitiostane, testolactone; anti-adrenals, such as aminoglutethimide, mitotane, trilostane; folic acid replenisher, such as folinic acid; aceglatone; aldophosphamide glycoside; aminolevulinic acid; eniluracil; amsacrine; bestrabucil; bisantrene; edatraxate; defosfamide; demecolcine; diaziquone; elformithine; elliptinium acetate; epothilone; etoglucid; gallium nitrate; hydroxyurea; lentinan; lonidamine; maytansinoids, such as maytansine and ansamitocin; mitoguazone; mitoxantrone; mopidamol; nitracrine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran (sizofiran); spirogermanium; tenuazonic acid; triaziquone; 2,2',2''-trichlorotriethylamine; trichothecenes (especially T-2 toxin, verrucarin A, roridin A and anguidin); urethan; vindesine; dacarbazine; mannomustine; mitobronitol; mitolactol; pipobroman; gacytosine; arabinoside ("Ara-C"); cyclophosphamide; thiotepa; taxoids, such as TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.) and TAXOTERE® docetaxel (Rhone-Poulenc Rorer, Antony, France); chlorambucil; GEMZAR® gemcitabine; 6-thioguanine; mercaptopurine; methotrexate; platinum analogues, such as cisplatin, oxaliplatin, and carboplatin; vinblastine; platinum; etoposide (VP-16); ifosfamide; mitoxantrone; vincristine; NAVELBINE, vinorelbine; novantrone; teniposide; edatrexate; daunomycin; aminopterin; xeloda; ibandronate; irinotecan (Camptosar, CPT-11) (a treatment regimen including irinotecan and 5-FU as well as leucovorin); topoisomerase inhibitor RFS 2000; difluoromethylornithine (DMFO); retinoids, such as retinoic acid, capecitabine; combretastatin; leucovorin (LV); oxaliplatin, including oxaliplatin treatment regimen (FOLFOX); lapatinib (TYK-ERB.); inhibitors of PKC-alpha, Raf, H-RasVEGF-A; and pharmaceutically acceptable salts, acids or derivatives of any of the above-mentioned substances.

The pharmaceutical composition described herein may be specifically formulated for administering a compound to a subject in solid, liquid, or gel form, including those suitable for the following forms: (1) parenteral administration, for example, acting as a sterile solution or suspension or sustained release formulation by way of e.g. subcutaneous, intramuscular, intravenous, or epidural injection; (2) surface application, for example, acting as cream, ointment or controlled release patch or spray administered to the skin; (3) intravaginal or intrarectal administration, for example, acting as pessary, emulsifiable paste, or foam; (4) eye administration; (5) percutaneous administration; (6) transmucosal administration; or (7) nasal administration.

In an aspect, the present disclosure relates to the use of an antibody or antibody fragment, a bispecific antibody, an antibody conjugate, or a pharmaceutical composition according to the present disclosure in the preparation of a drug for treating cancer. In some embodiments, the cancer is a HER2-positive cancer.

In another aspect, the present disclosure relates to the use of an antibody or antibody fragment, a bispecific antibody, an antibody conjugate, or a pharmaceutical composition according to the present disclosure for cancer treatment. In some embodiments, the cancer is a HER2-positive cancer.

In yet another aspect, the present disclosure relates to a method for treating cancer, comprising a step of administering an antibody or antibody fragment, a bispecific antibody, an antibody conjugate, or a pharmaceutical composition according to the present disclosure to a subject. In some embodiments, the cancer is a HER2-positive cancer.

Examples of cancers include but are not limited to: basal cell carcinoma, biliary tract cancer; bladder cancer; bone cancer; brain and CNS cancer; breast cancer; peritoneal cancer; cervical cancer; bile duct cancer; choriocarcinoma; colorectal cancer; cancer of connective tissue; cancer of digestive system; endometrial cancer; esophageal cancer; eye cancer; head and neck cancer; gastric cancer (including gastrointestinal cancer); glioblastoma; liver cancer; hepatoma; intraepithelial neoplasia; kidney cancer; laryngeal cancer; leukemia; hepatic carcinoma; lung cancer (e.g. small cell lung cancer, non-small cell lung cancer, lung adenocarcinoma, and lung squamous cell carcinoma); lymphoma, including Hodgkin's lymphoma and non-Hodgkin's lymphoma; melanoma; myeloma; neuroblastoma; oral cancer (such as lips, tongue, mouth, and pharynx); ovarian cancer; pancreatic cancer; prostate cancer; retinoblastoma; rhabdomyosarcoma; rectal cancer; cancer of respiratory system; salivary gland cancer; sarcoma; skin cancer; squamous cell carcinoma; gastric cancer; teratocarcinoma; testicular cancer; thyroid cancer; uterine or endometrial cancer; cancer of urinary system; vulvar cancer; and other cancers and sarcomas; and post-transplant lymphoproliferative disorder (PTLD), and abnormal vascular proliferation associated with phakomatosis, edema (such as edema associated with brain tumors), originally derived tumor, and Meigs's syndrome.

In some embodiments, the cancer is selected from breast cancer, gastric cancer, ovarian cancer, prostate cancer, and lung cancer.

DETAILED DESCRIPTION OF THE EMBODIMENTS

The contents of the present disclosure will be further described below with reference to examples. It should be understood that the following examples are merely illustrative and shall not be deemed as limiting the scope of the present disclosure.

Example 1: Construction of Bispecific Antibody

1. Construction of a First Heavy Chain that Binds to Tumor Antigens

Referring to the amino acid sequence of monoclonal antibody Ch4D5 (PDB Database #1N8E), the inventors designed and constructed a ScFv structure binding to the tumor target Her2/neu as a first binding domain of the bispecific antibody, and several forms were further designed, such as VH-linker-VL, VL-linker-VH, and VH-linker-VL plus L234A and L235A mutations. Specific designs are as follows:

In a first embodiment, the scFv that binds to the tumor target Her2 was formed by connecting, from the N-terminus to the C-terminus, VH of the anti-Her2 antibody Ch4D5 with an oligopeptide linker (GGGGS)×3 of 15 amino acids (SEQ ID NO: 23), and then with VL of Ch4D5. The obtained scFv was connected to the hinge region and the Fc having an OB mutation, hereby forming a ScFv-Fc heavy chain that binds to Her2, namely Her2-OB1 (SEQ ID NO: 1).

In a second embodiment, the scFv that binds to the tumor target Her2 was formed by connecting, from the N-terminus to the C-terminus, VL of Ch4D5 with an oligopeptide linker (GGGGS)×3 of 15 amino acids (SEQ ID NO: 23), and then with VH of Ch4D5. The obtained scFv was connected to the hinge region and the Fc having an OB sequence, hereby forming a ScFv-Fc heavy chain that binds to Her2, namely Her2-OB2 (SEQ ID NO: 3).

In a third embodiment, the structure of the ScFv-Fc heavy chain that binds to the tumor target Her2 was similar to that in the first embodiment, that is, VH of the anti-Her2 antibody Ch4D5 was connected with an oligopeptide linker (GGGGS)×3 of 15 amino acids (SEQ ID NO: 23), and then connected with VL of Ch4D5. The obtained scFv was connected to the hinge region and the Fc having an OB sequence. Since NcoI and Bgl II multiple cloning sites were contained between the VL region and the hinge region of Her2-OB1 (SEQ ID NO: 1), an additional amino acid TVAMVR (SEQ ID NO: 24) was contained. In this embodiment, this sequence was replaced with the human antibody sequence GEPK (SEQ ID NO: 25), hereby forming a ScFv-Fc heavy chain that binds to Her2, i.e. Her2-OB3 (SEQ ID NO: 5).

In a fourth embodiment, L234A and L235A mutations were introduced into the CH2 region of the heavy chain of the monoclonal antibody Ch4D5 on the basis of the third embodiment, so as to reduce the ADCC function and the CDC function of the antibody to avoid damages to T cells. The obtained sequence was Her2-OB4 (SEQ ID NO: 7).

From the ELISA results, it could be determined that the above four constructs all showed high affinity for Her2/neu, wherein 0131, 0B3, and 0B4 with a VH-linker-VL structure showed higher affinity than 0B2 with a VL-linker-VH structure.

2. Construction of Heavy Chain and Light Chain Variable Domains that Bind to T cell surface antigen CD3

The inventors conducted deep analysis and comparison of multiple murine antibodies against human CD3 complex, and sequential optimization and humanized modification were performed for variable domains of the murine antibody GXP (SP34) therein.

GXP (SP34) is a murine monoclonal antibody against human CD3, and humanized modification thereto has been reported (see U.S. Pat. No. 9,587,021, PCT/US20121038219). The inventors performed humanized modification on the VH and VL framework sequences thereof and kept the CDR1, CDR2 and CDR3 sequences of the murine heavy chain and light chain unchanged. Another important modification principle is to keep the murine sequence near each CDR region as much as possible, so as to reduce the influence on the structural stability of the antibody and on the affinity for the antigen.

The final sequence determined by the inventors is shown in Table 1A and Table 1B, and is named as GXP2.

TABLE 1A

VH Sequence

```
C31   E V Q L V E S G G G L V Q P G G S L R L S C A A S G F T F N
GXP   E V K L L E S G G G L V Q P K G S L K L S C A A S G F T F N
GXE2  E V Q L V E S G G G L V Q P G G S L K L S C A A S G F T F N

C31   T Y A M N W Y R Q A P G K G L E W V A R I R S K Y N N Y A T
GXP   T Y A M N W V R Q A P G K G L E W V A R I R S K Y N N Y A T
GXP2  T Y A M N W V R Q A P G K G L E W V A R I R S K Y N N Y A T

C31   Y Y A D S V K D R F T I S R D D S K N S L Y L Q M N S L K
GXP   Y Y A D S V K D R F T I S R D D S Q S I L Y L Q M N N L K
GXP2  Y Y A D S V K D R F T I S R D D S K N T A Y L Q M N N L K

C31   T E D T A V Y Y C A R H G N F G N S Y V S W F A Y W G Q G
GXP   T E D T A M Y Y C V R H G N F G N S Y V S W F A Y W G Q G
GXP2  T E D T A M Y Y C V R H G N F G N S Y V S W F A Y W G Q G

C31   T L V T V S S
      (SEQ ID NO: 26)
GXP   T L V T V S S
      (SEQ ID NO: 27)
GXP2  T L V T V S S
      (SEQ ID NO: 21)
```

TABLE 1B

VL Sequence

```
C31   Q A V V T Q E P S L T V S P G G T V T L T C G S S T G A V
GXP   Q A V V T Q E S A L T T S P G E T V T L T C R S S T G A V
GXP2  D I Q M T Q E P S L T T S P G G T V T L T C R S S T G A V

C31   T T S N Y A N W V Q E K P G Q A P R G L I G G T N K R A
GXP   T T S N Y A N W V Q E K P D H L F T G L I G G T N K R A
GXP2  T T S N Y A N W V Q E K P G Q A P R G L I G G T N K R A

C31   P W T P A R F S G S L L G G K A A L T I T G A Q A E D E A D
GXP   P G V P A R F S G S L I G D K A A L T I T G A Q T E D E A I
GXP2  P G T P A R F S G S L I G G K A A L T I T G V Q P E D E A I

C31   Y Y C A L W Y S N L W V F G G G T K L T V L G (SEQ ID NO: 28)
GXP   Y F C A L W Y S N L W V F G G G T K L T V L   (SEQ ID NO: 29)
GXP2  Y F C A L W Y S N L W V F G G G T K L         (SEQ ID NO: 30)
```

The inventors used the murine sequence of GXP (SP34), the humanized GXP2 sequence, and a humanized sequence (named as C31) disclosed in U.S. Pat. No. 9,587,021 to construct bispecific antibodies Her2×GXP, Her2×GXP2 and Her2×C31, and the thermal stability and biological activity thereof were compared. It is surprisingly found according to the results that the affinity of GXP2 for human CD3 is improved in comparison with the murine GXP and the humanized sequence C31, and the thermal stability is also significantly increased ($\Delta T$ is greater than 12° C.); and the stability was kept and no degradation occurred after storage for 27 days at 37° C. and 40° C. or under condition of repeated freezing and thawing.

The tumor killing effect of the bispecific antibody and the activity of inducing cytokine storm were further evaluated, and the results showed that the capability of GXP2 for killing Her2-positive tumor cells was significantly improved, while the activity of inducing cytokine storm was greatly reduced in comparison with the anti-CD3 monoclonal antibody. Moreover, an excellent anti-tumor killing activity was exhibited in the transplanted tumor model in NOD-SCID mice. The above results showed that GXP2 is a potential anti-tumor drug candidate.

Example 2: Expression and Purification of Bispecific Antibodies

All the bispecific antibodies involved in this experiment were expressed by adopting transient transfection or stable transfection, and a Maxi Kit (OMEGA) was firstly used for plasmid extraction, and the specific preparation operations were carried out according to the conventional general molecular biotechnology. Shake-flask culture of 130 rpm was realized for 293F cells in OPM-CD03 293 culture medium at 37° C. with a 5% $CO_2$ Rocking Device; after that the cell growth entered the logarithmic growth phase, the 293F cells were co-transfected with different combinations of plasmids using a transfection reagent PEI, so as to express a series of anti-HER2×CD3 bispecific antibodies. Cell culture supplements were respectively added at 24 hours and 96 hours after transfection, and the cell culture supernatant was collected by centrifugation at 3500 rpm on the 7th day after transfection.

In the present disclosure, a Protein A affinity chromatographic column (GE) was utilized to capture the double antibody from the cell culture supernatant. The column was firstly equilibrated with 10 column volumes of equilibration buffer (PBS, PH 7.4), the sample was then loaded for flowing through the affinity chromatographic column, and then elution was performed with an elution buffer (100 mM glycine-HCl, pH 3.5, containing 150 mM sodium chloride). Cation-exchange chromatography was then performed, the mixture flowed through the Hitrap SP HP column (GE), such that the target bispecific antibody was separated from byproducts; and after that the column was equilibrated with an equilibration buffer (50 mM phosphate buffer, pH 6.0), gradient elution was performed with a mixture from the elution buffer of 50 mM phosphate buffer (pH 6.0, solution A), and 50 mM phosphate buffer containing 1M sodium chloride (pH 6.0, solution B), and washing was performed with 25 column volumes; and finally, storage was realized after concentration and replacement with PBS Buffer (pH 7.4).

Figures 2A, 2B:
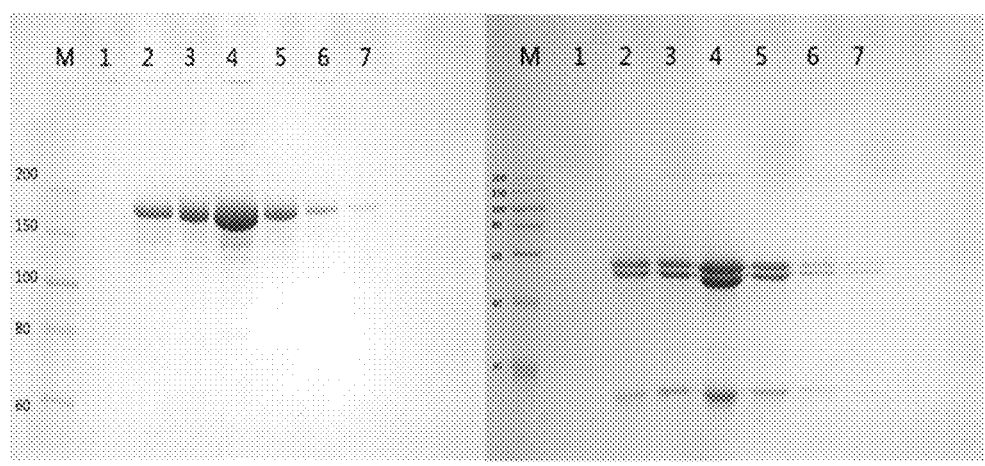
FIGS. 2A-2B show an SDS-PAGE electrophoretogram of a bispecific antibody purified with protein A.

Subsequently, the purified product was subjected to SDS-PAGE test and identification, and the results are shown in FIGS. 2A-2B. Herein, FIG. 2A shows the non-reducing SDS-PAGE result, and FIG. 2B shows the reducing SDS-PAGE result, wherein M represents the molecular weight marker of protein, and wells 2-7 represent eluted samples of the bispecific antibody HER2×GXP2 after Protein A purification. From the results in FIGS. 2A-2B, it can be seen that the target bispecific antibody with high purity can be obtained after one-step purification with Protein A. This indicates that the light chain can specifically bind to the homologous heavy chain without mismatching, thereby ensuring that the expression product contains a highly purified target bispecific antibody. Since the bispecific antibody disclosed in the present disclosure is of an asymmetric structure, the molecular weight of the target antibody is inconsistent with that of the corresponding homodimer, which is more conducive to downstream purification.

Example 3: Analysis of the Binding Activity of a Bispecific Antibody to Target Antigens CD3 and HER2

ELISA analysis was adopted in this study. The specific experimental steps were as follows: coating the antigen CD3 or the antigen HER2 on the enzyme-labeled plate (NUNC); coating at 4° C. and leaving the same overnight; adding skim milk for sealing after plate washing; then adding a bispecific antibody and a control sample after plate washing; incubating at room temperature for 1.5 hours; washing the plate, and then adding a 1:2000 diluted secondary antibody (peroxidase-conjugated goat anti-human IgG, Proteintech™), incubating at room temperature for 1 hour, washing the plate, and then adding luminescent substrate A+B (A:B=1:1); and detecting the absorbance on a microplate reader (Synergy HTX, BioTeck) after 3 minutes.

Figure 3:
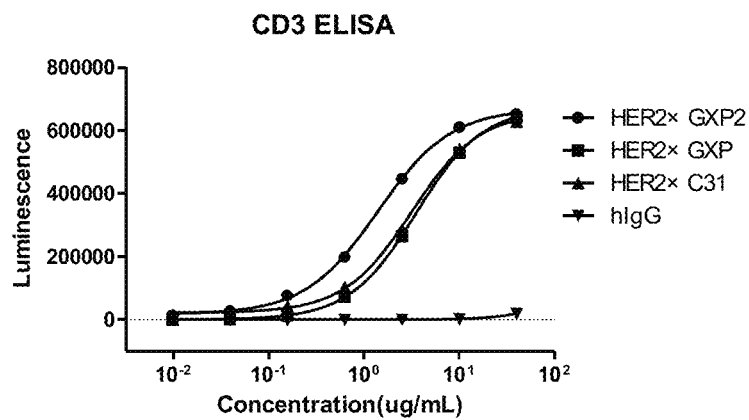
FIG. 3 shows ELISA test results of bispecific antibodies HER2×GXP2, HER2×GXP, and HER2×C31, as well as the control hIgG regarding the activity of binding the human CD3 antigen.

ELISA results showed that the bispecific antibody showed positive binding to CD3 antigen, and the binding rate presented a dose-dependent relationship. The binding activity of the humanized antibody HER2-OB1×GXP2 disclosed in the present disclosure to CD3 antigen is higher than that of the humanized antibody HER2-OB1×C31 and the murine antibody HER2-OB1×GXP, and the EC50s of the binding of the three to the CD3 antigen were respectively 1.402 μg/mL, 3.522 μg/mL, and 3.153 μg/mL (FIG. 3).

Figure 4:
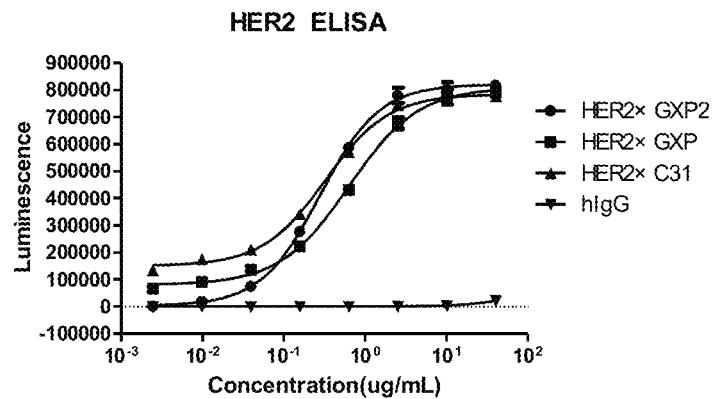
FIG. 4 shows ELISA test results of bispecific antibodies HER2×GXP2, HER2×GXP, and HER2×C31, as well as the control hIgG regarding the activity of binding the human HER2 antigen.

In addition, bispecific antibodies can also specifically recognize and bind to the surface antigen HER2 of tumor cells, and the binding rate presented a dose-dependent relationship. The binding activities of the bispecific antibodies HER2-OB1×GXP2, HER2-OB1×C31, and HER2-OB1×GXP to the HER2 antigen are more or less the same, indicating that the combination of the HER2 sequence with different CD3 antibody sequences does not affect its binding to the HER2 antigen (see FIG. 4).

Example 4: Thermal Stability Analysis of Bispecific Antibodies

1. Detection of the Stability and the Affinity of Bispecific Antibodies after Heat Treatment An appropriate amount of bispecific antibody samples was respectively dispensed into PCR tubes, 10 tubes for each sample, and a temperature gradient was set on the PCR instrument (Mygene™) for constant temperature heating for 30 min, and the temperature was respectively set at 35° C., 40.6° C., 45° C., 50° C., 55.6° C., 60° C., 65° C., 70.6° C., 75° C., while the remaining 1 tube of original antibody was stored at −20° C. as a control. After processing, the samples were cooled to room temperature and placed at −20° C. for standby application.

The enzyme-labeled plate was coated with CD3 antigen or HER2 antigen, sealed with milk after plate washing, and then washed; an original bispecific antibody for control and a heat-treated bispecific antibody were then added, and plate washing was performed after incubation for 1 hour; an enzyme-labeled antibody was then added, incubated, and plate washing was performed; a luminescent substrate reacting with the enzyme-labeled antibody was added; and then the absorbance was detected through a multifunctional microplate reader (Synergy HTX, BioTek), wherein this absorbance is proportional to the amount of the specifically bound antibody. The results showed that the midpoint $T_{50}$ of the heat denaturation curve of the HER2-OB1×GXP2 bispecific antibody reached 58.28° C.

Figure 5:
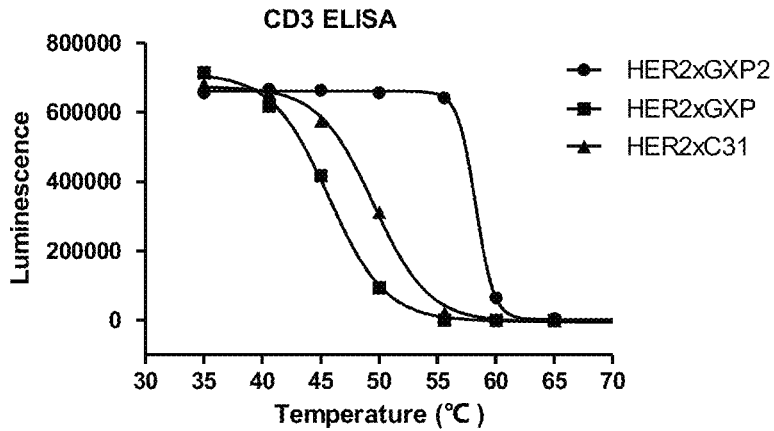
FIG. 5 shows the ELISA test results of bispecific antibodies HER2×GXP2, HER2×GXP, and HER2×C31 regarding the activity of binding the human CD3 antigen after being treated at different temperatures for 30 minutes. It reflects the thermal stability of bispecific antibodies at different temperatures.
Figure 6A:
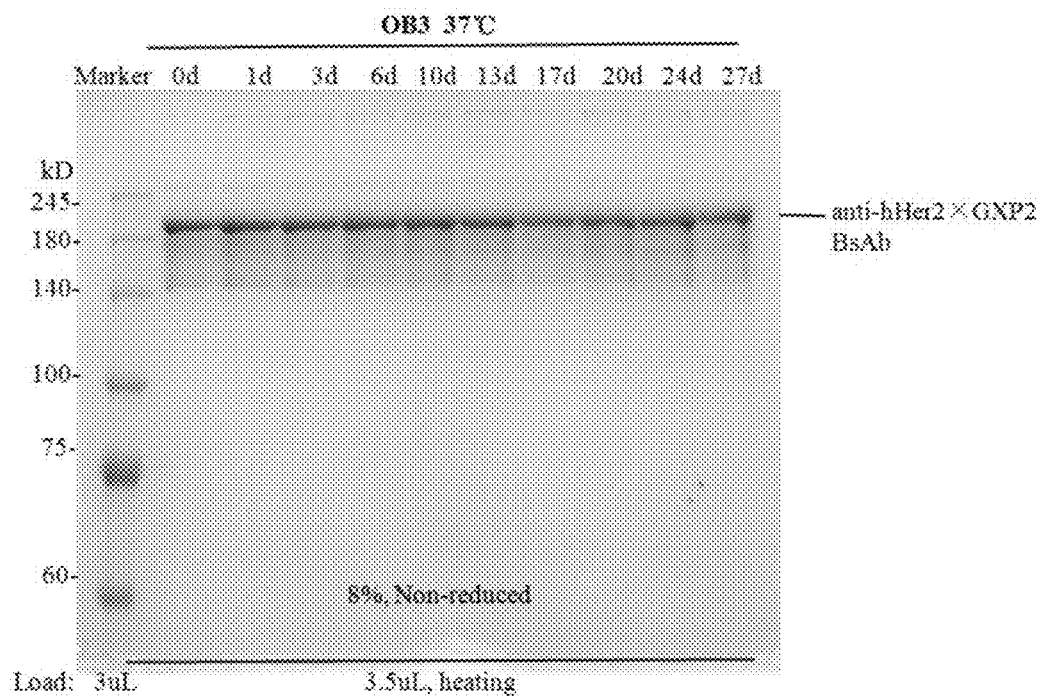
FIGS. 6A-6D show the stability and the degradation of bispecific antibodies detected through non-reducing and reducing SDS-PAGE, after respectively being placed in 37° C. and 40° C. incubators for different days.
Figure 6B:
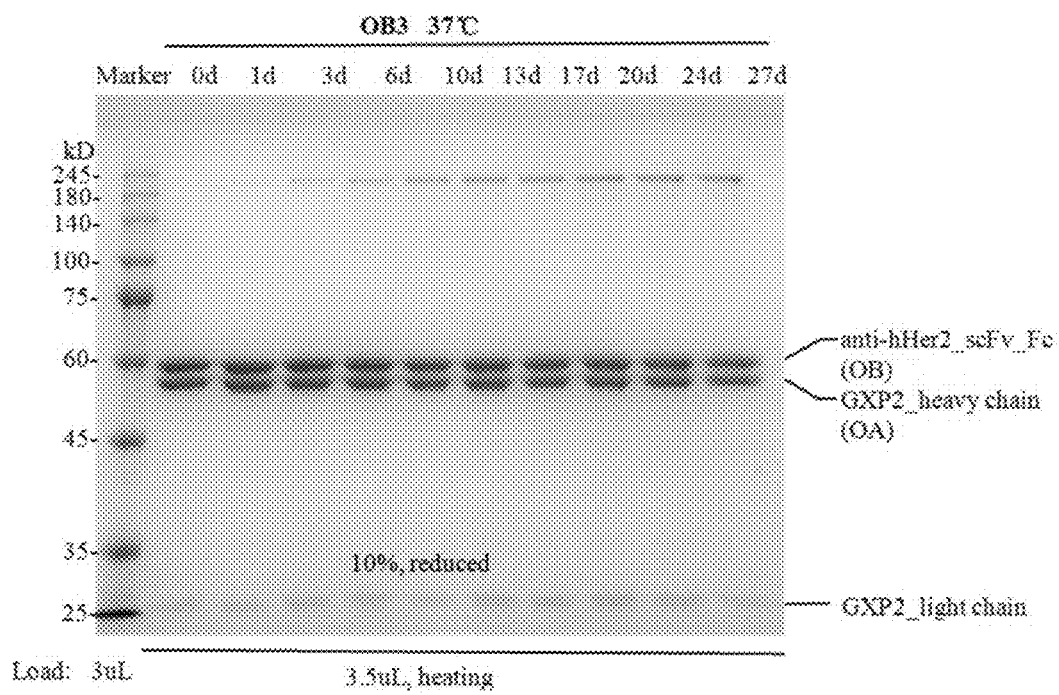
Figure 6C:
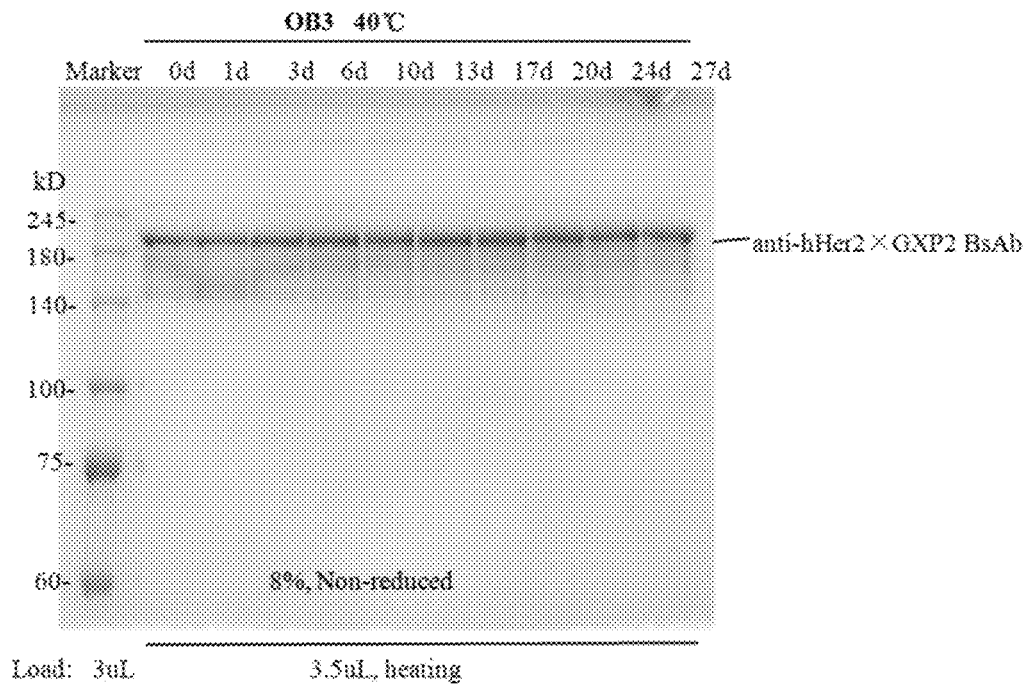
Figure 6D:
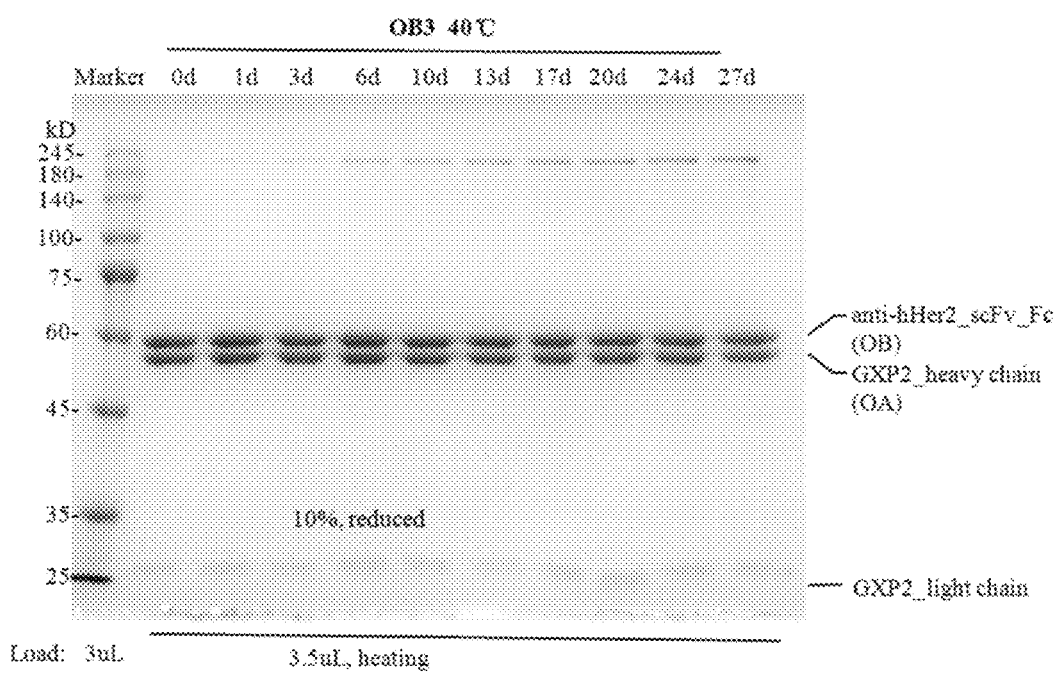

The bispecific antibody treated as described above was detected through ELISA regarding its binding ability to the CD3 antigen, so as to identify its thermal stability. The results showed that the thermal stability of the humanized antibody HER2-OB1×GXP2 according to the present disclosure was significantly improved, and the midpoint T50 of the thermal denaturation curve thereof reached 58.28° C., which was not only improved by about 12° C. in comparison with the murine antibody HER2-OB1×GXP (T50 was 45.71° C.), but also improved by almost 10° C. in comparison with another humanized bispecific antibody HER2-OB1×C31 (T50 was 49.55° C.) (see FIG. 5). These results indicated that after the optimization and the transformation according to the present disclosure, the thermal stability of HER2-OB1×GXP2 was significantly improved, which indicates a better suitableness for use as an antibody drug for treating cancer.

2. Long-Term Thermal Stability Test of Bispecific Antibodies

An appropriate amount of a bispecific antibody was dispensed into 20 1.5 mL EP tubes, and 10 tubes of which were then placed at 37° C., while the other 10 tubes were placed at 40° C. As for the two groups of experiment, a SDS-PAGE loading buffer was successively added to one of the tubes on day 0, day 1, day 3, day 6, day 10, day 13, day 17, day 20, day 24, and day 27, respectively, and then frozen at −20° C. Finally, the SDS-PAGE test was performed on all samples.

The electrophoretic results showed that no matter whether it was preserved at 37° C. or 40° C. for 27 days, the bispecific antibody HER2×GXP2 did not show significant degradation (see FIGS. 6A-6D). The above results indicated that the HER2×GXP2 bispecific antibody has good long-term stability.

3. Stability Test of Bispecific Antibodies after Repeated Freezing and Thawing

An appropriate amount of a bispecific antibody was dispensed into 4 1.5 mL EP tubes and labeled as F-T0-3, and F-TO was then placed at 4° C., and F-T1-3 was placed at −20° C. After that F-T1-3 was frozen as a solid, F-T1-3 was quickly melted, and F-T1 was placed at 4° C., and F-T2-3 was placed at −20° C. After that F-T2-3 was frozen as a solid, F-T2-3 was quickly melted and F-T2 was placed at 4° C., which was repeatedly frozen and thawed 2 times; and F-T3 was placed at −20° C. After that F-T3 was frozen as a solid, F-T3 was quickly melted, which was repeatedly frozen and thawed 3 times. Finally, the SDS-PAGE test and ELISA analysis were performed on all samples.

Figure 7A:
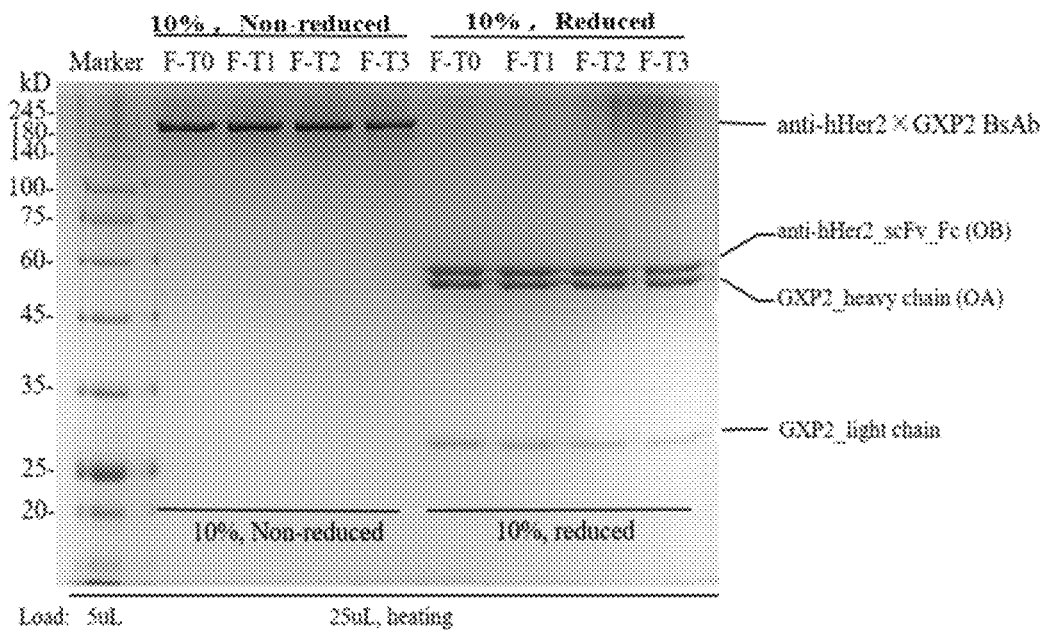
FIGS. 7A-7C show experimental results regarding the stability of bispecific antibodies after repeated freezing and thawing, detected through SDS-PAGE and ELISA.
Figure 7B:
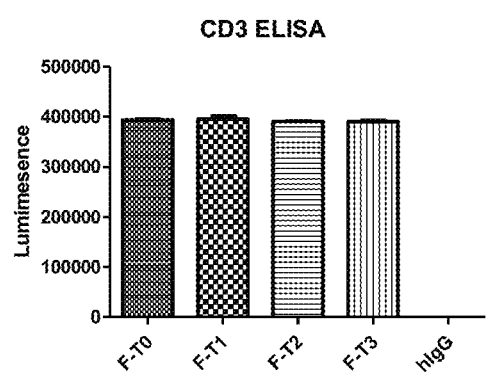
Figure 7C:
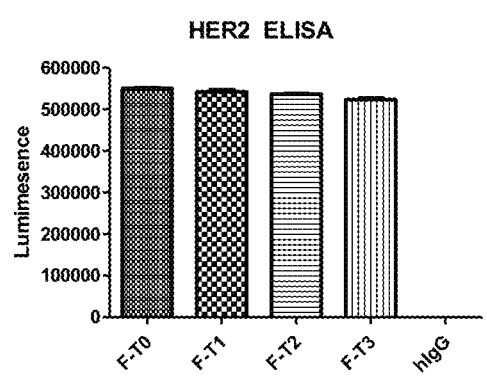
Figure 8A:
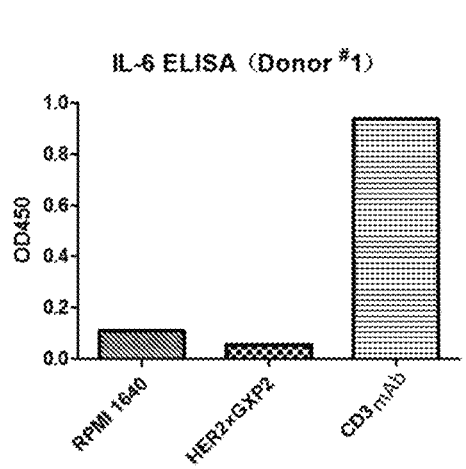
FIGS. 8A-8D show influences of bispecific antibodies on cytokine release. The ELISA results for the release of cytokines TNF-α and IL-6, after treatment with the bispecific antibody HER2×GXP2 and the control CD3 monoclonal antibody, in the PBMC samples from donor #1 and donor #2 are shown.
Figure 8B:
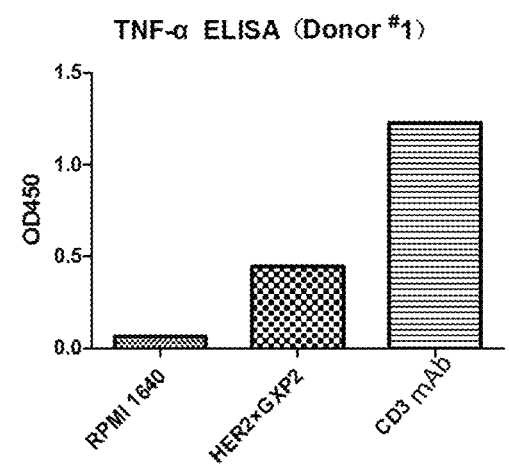
Figure 8C:
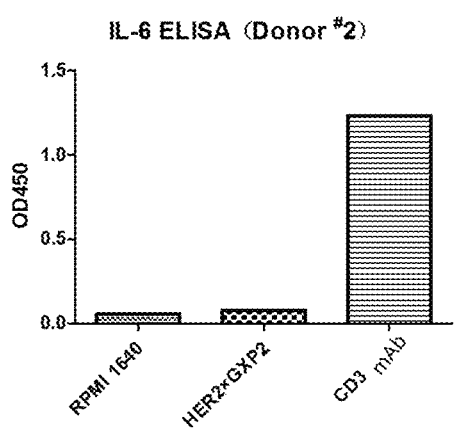
Figure 8D:
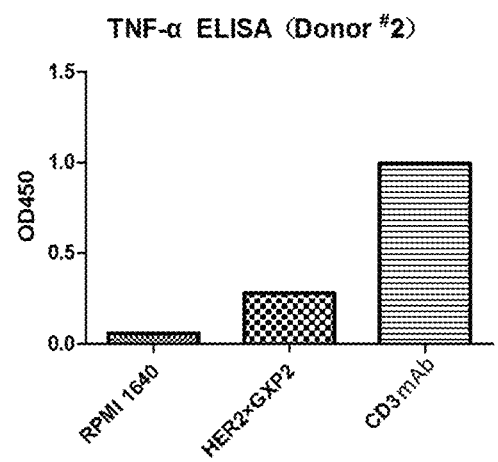

The SDS-PAGE results showed that after repeated freezing and thawing three times, the bispecific antibody HER2×GXP2 did not show significant degradation, and its strip remained consistent with the non-frozen-thawed sample (see FIG. 7A), which indicated the stability of the bispecific antibody under condition of repeated freezing and thawing. Consistent with this, in the ELISA tests of CD3 and HER2, the absorbance of the frozen and thawed samples and the absorbance of the non-frozen-thawed samples binding to corresponding antigens are basically identical with each other (see FIGS. 7B and 7C), indicating that in the case of repeated freezing and thawing, the bispecific antibody HER2×GXP2 retained a high binding activity to CD3 antigen and HER2 antigen.

Example 5: Influences of Bispecific Antibodies on Cytokine Release

In the present disclosure, the influence of bispecific antibodies on cytokine release was measured by using PBMC cells. The PBMC cells were washed with PBS, and then the cell density was adjusted to $2\times10^6$/mL with 1640 culture medium, and then added to a 96-well plate at 100 μL/well, that is, $2\times10^5$ cells/well. The antibody was diluted to 2 μg/mL with 1640 culture medium, and 100 μL diluted solution of the antibody was then added to each well, that is, the final antibody concentration was 1 μg/mL, and the 96-well plate was placed in a 37° C., 5% $CO_2$ incubator for cultivation for 24 hours. In this experiment, the double antibody sandwich ELISA method was used to test the concentration of cytokines in the samples. The monoclonal capture antibody that specifically binds to cytokines has been coated on the enzyme-labeled plate, and the cytokines in the samples would bind to the capture antibody. Subsequently, the biotinylated anti-cytokine antibody binds to cytokines to form an immune complex of capture antibodies, cytokines, and biotinylated antibodies. The specific experimental steps were as follows: centrifuging the above 96-well plate containing PBMC cells at 1000 rpm for 5 min, adding the supernatant at 100 μL/well into the corresponding well, sealing the reaction well with a sealing film, and incubating at room temperature for 120 minutes. Plate washing was performed 5 times, a biotinylated antibody was added at 100 μL/well, the reaction well was sealed with a sealing film, and incubation was performed at room temperature for 60 minutes. Plate washing was performed 5 times, HRP-streptavidin was added at 100 μL/well, the reaction well was sealed with a sealing film, and lucifugal incubation was performed at room temperature for 10-20 minutes; and plate washing was performed 5 times, the chromogenic agent TMB solution was added at 100 μL/well, the reaction well was sealed with a sealing film, and lucifugal incubation was performed at room temperature for 20 minutes. A stop solution was added at 50 μL/well, the absorbance at 450 nm was tested with a microplate reader immediately after thorough mixing. The experimental results are shown in FIGS. 8A-8D.

An equal amount of HER2×GXP2 antibodies or CD3 monoclonal antibodies are used for co-incubation with PBMC from different healthy donors and stays overnight, the supernatant thereof was taken for performing the experiment of the above-mentioned ELISA sandwich method, and the amount of released cytokines IL-6 and TNF-α was tested, so as to identify whether T cells were non-specifically activated and produced a cytokine storm. The experimental results showed that in the absence of HER2-positive cells, high-dose (1 μg/mL) HER2×GXP2 antibody was used for co-incubation with PBMC of different donors, and no non-specific activation of T cells occurred. The CD3 monoclonal antibody led to high-level release of cytokines, including IL-6 and TNF-α, which proved that the T cells used in this experiment were normally functional and could be activated by the CD3 monoclonal antibody. In contrast, the bispecific antibody HER2×GXP2 according to the present disclosure showed similar levels of IL-6 and TNF-α to the negative control group (RPMI 1640 culture medium), which were both significantly lower than that in the group of the CD3 monoclonal antibody; and the use of PBMC from different donors achieved similar results (FIG. 8A and FIG. 8B respectively showed results of IL-6 and TNF-α of donor #1; while FIG. 8C and FIG. 8D respectively showed results of IL-6 and TNF-α of donor #2). The above results indicated that the occurrence of cytokine storms could be reduced, and the safety thereof would be also greatly improved, if the HER2×GXP2 double antibody of the present disclosure is used clinically for treating HER2-positive tumors.

Example 6: Measurement of Killing HER2-Positive Tumor Cell by Bispecific Antibody-Mediated PBMC Cells 1. Cultivation of Target Cells SKBR cells (HER2+++), N87 cells (HER2++), and MCF-7 cells (HER2+) were cultured in T75 culture flasks and placed in a 37° C., 5% $CO_2$ incubator for cultivation. The culture media corresponding to the above cells were as follows: SKBR-3: DMEM (Gibco), N87: 1640 (Gibco), and MCF-7: MEM (Gibco); and the culture media all contained 10% FBS, 1× GlutaMax-I and 100 U/mL double antibiotics. 293F cells (HER2-negative) acting as control were cultured in OPM CD03 293 culture medium in a 37° C., 5% $CO_2$ Rocking Device.

2. Separation of PBMC

After collecting fresh whole blood intravenously, the fresh whole blood was diluted with normal saline 2 times, lymphocytes separating solution was extracted and transferred into a graduated centrifuge tube, and the diluted whole blood was slowly added with a dropper along the tube wall onto the separating medium, so as to keep a clear interface between the two. The centrifuging was performed at 760 g with a horizontal centrifuge for 30 min. The position of the buffy coat was observed, a capillary pipette was gently inserted into the turbidity zone, and cells in this layer were gently sucked out with a dropper and transferred into another centrifuge tube (avoiding sucking out too much separating solution or plasma, so as to avoid mixing with other cellular constituents). The cells were washed 3 times with PBS and horizontally centrifuged at room temperature, wherein the centrifuging was performed at 427 g for 15 min for the first time, the centrifuging was performed at 273 g for 10 min for the second time, and the centrifuging was performed at 229 g for 10 min for the third time, and most of mixed platelets can then be removed. The cells were suspended in 1640 culture medium (containing 10% FBS and double antibody) and cultured in a 37° C., 5% $CO_2$ incubator.

3. ADCC (Antibody-Dependent Cell-Mediated Cytotoxicity)

This study was based on the following principle that the bispecific antibody binds to target cells and T cells, which simultaneously recognized the HER2-positive target cells and CD3 complex on T cells were simultaneously recognized, such that tumor cells and T cells were in close to each other, thereby activating T cells to kill tumor cells. In the present disclosure, LDH release experiment was employed to test the killing activity of the bispecific antibody, that is to say, the lactate dehydrogenase in the cells was released into the supernatant, and a certain amount of the supernatant was taken and added into the reaction substrate lactic acid and an appropriate amount of enzyme solution, wherein the lactate dehydrogenase reacted with lactic acid; and the tumor cell killing activity of PBMC stimulated by the antibody can be indirectly measured by determining the amount of lactate dehydrogenase released by tumor cells through the absorbance measurement.

The target cells (including SKBR-3 cells, NCI-N87 cells, and MCF-7 cells) were digested with the pancreatic enzyme to prepare a single-cell suspension, and the single-cell suspension was already formed when culturing 293F cells. The cell concentration was adjusted to $0.20×10^6$/mL with 5% FBS-1640 culture medium, and added to a 96-well plate at 50 μL/well, such that each well contained $1.0×10^4$ cells. The ratio between effector cells and target cells used in the present experiment was 15: 1. A control well was set in the experiment, in which a 5% FBS-1640 culture medium of the same volume was filled up.

The antibody was diluted to 4 μg/mL with a 5% FBS-1640 culture medium, and then a doubling dilution was performed in a ratio of 1:4 to obtain 10 antibodies respectively having a concentration of 4000 ng/mL, 1000 ng/mL, 2500 ng/mL, 625 ng/mL, 156.25 ng/mL, 39.06 ng/mL, 9.77 ng/mL, 2.44 ng/mL, 0.61 ng/mL, and 0.15 ng/mL. According to the experimental design, corresponding antibodies were added at 50 μL/well, and the control well was filled up with an isometric 5% FBS-1640 culture medium. The cells and the antibody were mixed uniformly and then incubated in a 37° C., 5% $CO_2$ incubator. After 18-20 hours, the killing toxicity of cells was tested using a lactate dehydrogenase cytotoxicity kit (Beyotime), and the killing activity of the double antibody was calculated accordingly, and the calculation formula was as follows:

Killing rate %=(experimental value−$S_{spontaneous}$)/ (Max−$S_{spontaneous}$)×100%

Herein, $S_{spontaneous}$=
$OD_{spontaneous\ release\ well\ (target\ cell+effector\ cell)}$,
Max=$OD_{maximum\ release\ well\ (target\ cell)}$ Tumor cell lines with different expression levels of HER2 were used for co-incubation with PBMC from healthy human and gradient-diluted HER2×GXP2, and the killing status of tumor cells was determined by measuring the content of lactate dehydrogenase in the supernatant. The results showed that the bispecific antibody HER2×GXP2 of the present disclosure had a very good killing effect on tumor cells with high expression of HER2, and also had a killing effect on tumor cells with low expression of HER2, but had no killing activity for HER2-negative cells. It indicated that the bispecific antibody showed good killing effect on HER2-positive tumor cells in in vitro cytotoxicity experiments, but had no killing effect on HER2-negative cells.

Figure 9A:
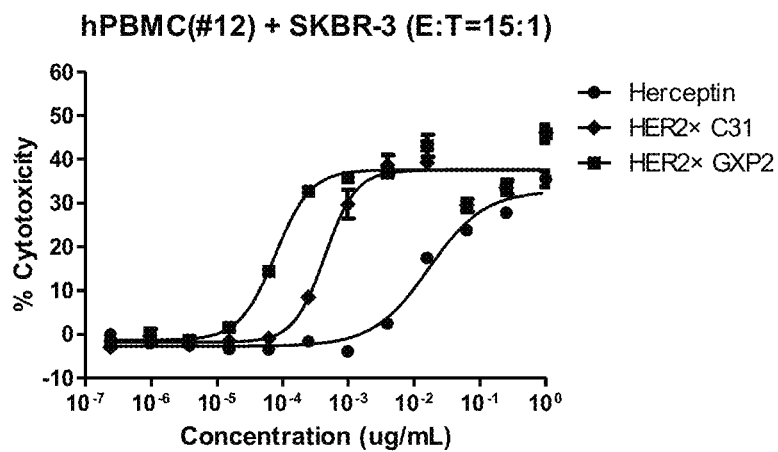
FIGS. 9A-9D show results of in vitro tumor killing experiments of T cells mediated by bispecific antibodies of different concentrations.

Specifically, human breast cancer cell SKBR-3 belongs to a cell line with high expression of HER2 antigen (HER2+++). HER2×GXP2 could effectively mediate in the killing of SKBR-3 by immune cells, and its EC50 was 5 times lower than that of another humanized antibody HER2×C31, and over 100 times lower than that of Herceptin, a currently clinically used breast cancer treatment drug (see FIG. 9A).

Figure 9B:
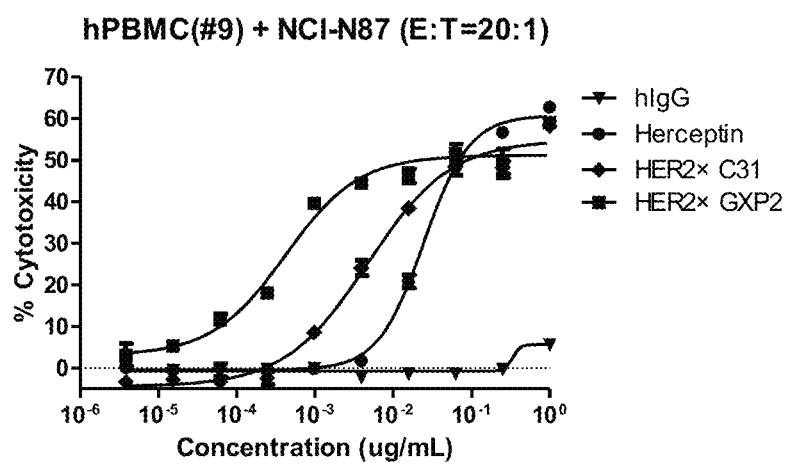

The human gastric cancer cell NCI-N87 (HER2++) had a slightly lower HER2 expression than SKBR-3 cells, wherein the EC50 of HER2×GXP2 was $3.952×10^{-4}$ μg/mL, which was significantly lower than that of Herceptin and HER2× C31 in the control groups (being respectively $2.182×10^{-2}$ μg/mL and $3.647×10^{-3}$ μg/mL) (see FIG. 9B), and had a trend being consistent with the results in SKBR-3 cells.

Figure 9C:
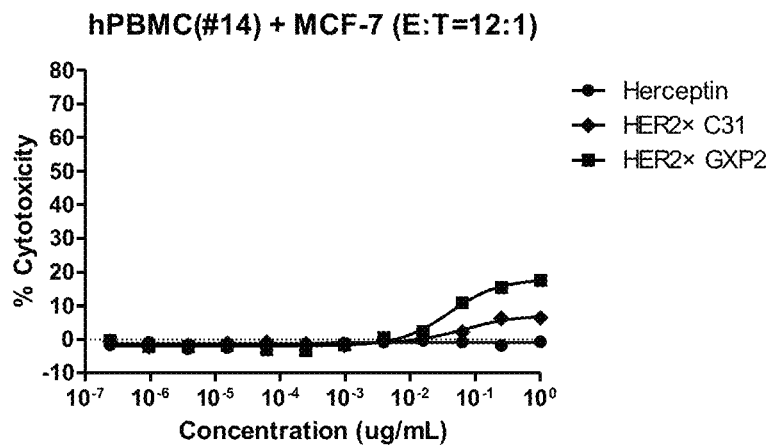
Figure 9D:
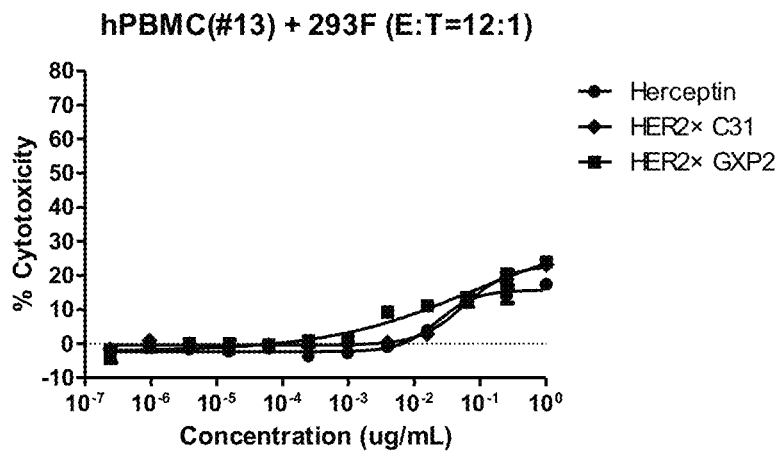

Cell lines with low expression of HER2 antigen or HER2-negative cell lines, such as MCF-7 cells and 293F cells (HER2+/−, equivalent to normal cells), were not sensitive to the killing mediated by the bispecific antibody HER2×GXP2, which had no obvious killing effect (see FIG. 9C and FIG. 9D).

In summary, tumor cells with high expression of HER2, such as SKBR-3 and NCI-N87 cells, were very sensitive to the anti-HER2×CD3 bispecific antibody HER2×GXP2, and the use of HER2×GXP2 at a lower concentration could achieve very good killing effect; moreover, the EC50 representing the killing effect of the bispecific antibody HER2×GXP2 disclosed herein on SKBR-3 and NCI-N87 cells was significantly lower than that of Herceptin and HER2×C31, indicating that the use of HER2×GXP2 at a lower concentration could achieve similar killing effect to that of Herceptin at a high concentration.

Besides, the bispecific antibody HER2×GXP2 had no obvious killing effect on cells with low expression of HER2 or HER2-negative cells, such as MCF-7 and 293F cells, and in combination with the killing effect of HER2×GXP2 on SKBR-3 and NCI-N87 cells, it is indicated that HER2×GXP2 could stimulate immune cells to specifically kill HER2-positive tumor cells, without damaging normal cells.

Figure 10:
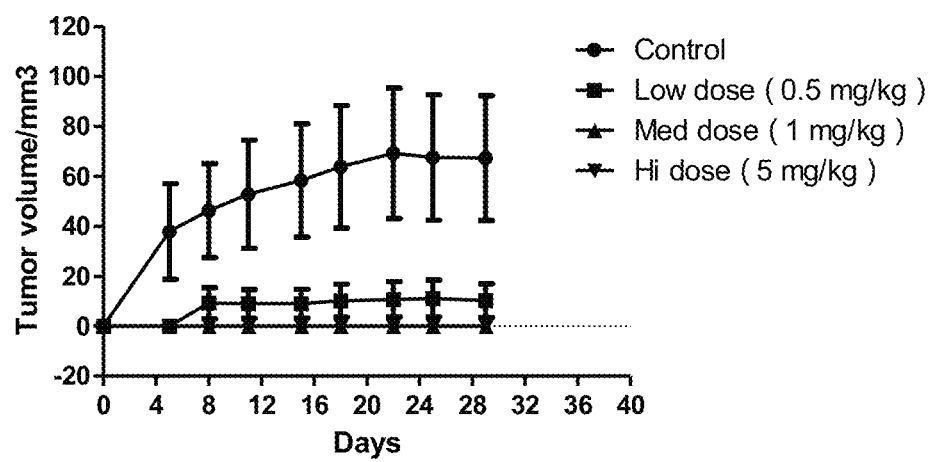
FIG. 10 shows results of in vivo tumor growth inhibition of bispecific antibodies with different doses in an animal tumor model.

Example 7: Analysis of the In Vivo Tumor Killing Effect of Bispecific Antibodies in Animal Tumor Models 24 mice were randomly divided into 4 groups, 6 in each group. After grouping the animals, SKOV-3 cells in the logarithmic growth phase (the Her2 expression level of HER2-positive ovarian cancer cells was between Her2$^{++}$ and Her2$^{+++}$) were collected and centrifuged; and the cell concentration of SKOV-3 cells was adjusted to $5\times10^7$ cells/mL, and the concentration of PBMC cells was adjusted to $5\times10^7$ cells/mL. SKOV-3 cells were mixed at an equal volume with PBMC and then inoculated subcutaneously in the right armpit of mice at 0.2 mL per mouse. After inoculation of tumor cells, the bispecific antibody HER2×GXP2 of the present disclosure was administered once a day on day 1, day 3, day 5, and day 8, respectively, at low dose (0.5 mg/kg), medium dose (1 mg/kg), and high dose (5 mg/kg) according to the grouping. The negative control group was given an isometric sterile saline. The long diameter and the short diameter of the tumor were measured and recorded once during grouping (i.e. before the first administration), twice a week after administration, and once before euthanasia; the tumor volume was calculated; and the tumor growth curve was drawn according to the tumor volume, and the differences of tumor growth curves of individual groups were compared. Tumor volume was calculated according to the following formula: $V=\frac{1}{2}\times\text{long diameter}\times\text{short diameter}^2$. FIG. 10 shows the curve of tumor volume changing with time.

The above results showed that the bispecific antibody HER2×GXP2 of the present disclosure effectively inhibited the tumor growth in mice's body, no matter whether it was administered at low dose, medium dose, or high dose. The above results proved that the bispecific antibody HER2×GXP2 of the present disclosure not only mediates immune cell in effective targeted killing of HER2-positive tumor cells in vitro, but also can effectively inhibit the growth of HER2-positive tumors in vivo.

---

The invention claimed is:

1. An antibody or antibody fragment, comprising an antigen binding domain that binds to CD3, wherein the antigen binding domain comprises a heavy chain variable domain (VH) having an amino acid sequence of SEQ ID NO: 21 and a light chain variable domain (VL) having an amino acid sequence of SEQ ID NO: 22.

2. The antibody or antibody fragment according to claim 1, comprising a heavy chain sequence of SEQ ID NO: 9 and a light chain sequence of SEQ ID NO: 11.

3. The antibody or antibody fragment according to claim 1, wherein the antibody is a bispecific antibody or a multispecific antibody.

4. The antibody or antibody fragment according to claim 1, further comprising an antigen binding domain for binding to an antigen target of a tumor.

5. The antibody or antibody fragment according to claim 4, wherein the antigen target of a tumor is HER2.

6. The antibody or antibody fragment according to claim 5, wherein the antibody comprises a heavy chain sequence selected from the group consisting of Her2-OB1 (SEQ ID NO: 1), Her2-OB2 (SEQ ID NO: 3), Her2-OB3 (SEQ ID NO: 5), and Her2-OB4 (SEQ ID NO: 7).

7. The antibody or antibody fragment according to claim 6, wherein the antibody comprises a heavy chain sequence of Her2-OB4 (SEQ ID NO: 7).

8. The antibody or antibody fragment according to claim 1, wherein the antibody fragment is selected from the group consisting of a Fab fragment, a Fab' fragment, a Fd fragment, a Fd' fragment, a Fv fragment, a dAb fragment, a F(ab')2 fragment, and a scFv fragment.

9. A bispecific antibody, comprising a first heavy chain, a second heavy chain, and a light chain, wherein the first heavy chain has a scFv-hinge region-Fc from an N-terminus to a C-terminus; the second heavy chain has a VH-CH1-hinge region-Fc from an N-terminus to a C-terminus; and the light chain has a VL-CL from an N-terminus to a C-terminus; wherein an antigen binding domain of the scFv of the first heavy chain binds to an antigen target of a tumor, and the VH-CH1 of the second heavy chain and the VL-CL of the light chain form an antigen binding domain, which binds to a signal channel receptor on a surface of an immune effector cell; wherein the VH of the second heavy chain has a sequence of SEQ ID NO: 21, and the VL of the light chain has a sequence of SEQ ID NO: 22.

10. The bispecific antibody according to claim 9, wherein the second heavy chain comprises a sequence of SEQ ID NO: 9, and the light chain comprises a sequence of SEQ ID NO: 11.

11. The bispecific antibody according to claim 9, wherein the scFv of the first heavy chain comprises, from N-terminus to C-terminus, a VH region of a Ch4D5-monoclonal antibody, a connecting peptide and a VL region of the Ch4D5-monoclonal antibody; or comprises, from N-terminus to C-terminus, the VL region of a Ch4D5-monoclonal antibody, the connecting peptide and the VH region of the Ch4D5-monoclonal antibody.

12. The bispecific antibody according to claim 9, wherein the first heavy chain comprises a sequence selected from the group consisting of Her2-OB1 (SEQ ID NO: 1), Her2-OB2 (SEQ ID NO: 3), Her2-OB3 (SEQ ID NO: 5) and Her2-OB4 (SEQ ID NO: 7).

13. The bispecific antibody according to claim 9, wherein the first heavy chain comprises the sequence of Her2-OB4 (SEQ ID NO: 7).

14. The bispecific antibody according to claim 9, wherein the CH2 of the first heavy chain is the CH2 of a heavy chain of a Ch4D5-monoclonal antibody containing L234A and L235A mutations.

15. The bispecific antibody according to claim 9, wherein the first heavy chain, the second heavy chain, and/or the light chain are derived from IgG1, IgG2, IgG3 or IgG4.

16. The bispecific antibody according to claim 11, wherein the connecting peptide is (GGGGS)×N, N=3, 4 or 5 (SEQ ID NO:s 23, 31, and 32 respectively).

* * * * *

SEQUENCE LISTING

```
<160> NUMBER OF SEQ ID NOS: 32

<210> SEQ ID NO 1
<211> LENGTH: 478
<212> TYPE: PRT
<213> ORGANISM: Artificial sequence
<220> FEATURE:
<223> OTHER INFORMATION: Her2-OB1 heavy chain

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Val Met Thr Gln Ser Pro Ser
    130                 135                 140
```

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
            165                 170                 175

Lys Ala Pro Lys Leu Leu Ile Tyr Ser Ala Ser Phe Leu Tyr Ser Gly
        180                 185                 190

Val Pro Ser Arg Phe Ser Gly Ser Arg Ser Gly Thr Asp Phe Thr Leu
    195                 200                 205

Thr Ile Ser Ser Leu Gln Pro Glu Asp Phe Ala Thr Tyr Tyr Cys Gln
210                 215                 220

Gln His Tyr Thr Thr Pro Pro Thr Phe Gly Gln Gly Thr Lys Val Glu
225                 230                 235                 240

Ile Lys Arg Thr Val Ala Ser Met Val Arg Ser Asp Lys Thr His Thr
                245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365

Lys Ala Lys Gly Gln Pro Arg Glu Pro Gln Val Tyr Thr Leu Pro Pro
    370                 375                 380

Ser Arg Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Asp Asp Asp Val Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475

<210> SEQ ID NO 2
<211> LENGTH: 1434
<212> TYPE: DNA
<213> ORGANISM: Artificial sequence
<220> FEATURE:
<223> OTHER INFORMATION: DNA sequence of Her2-OB1 heavy chain

<400> SEQUENCE: 2
gaggtgcagc tggtggaatc cggaggcgga ctggtgcagc ctggaggaag cctgagactg     60
agctgcgccg ccagcggctt caacatcaag gacacctata tccattgggt gaggcaggct    120
cccggaaaag gcctggagtg ggtggccagg atctacccta ccaacggcta caccaggtac    180

```
gccgacagcg tgaagggcag gttcaccatc agcgccgaca ccagcaagaa caccgcctac    240
ctgcagatga acagcctcag agccgaggac accgccgtgt attactgcag cagatggggc    300
ggcgacggct tctacgctat ggattactgg ggacagggca cactggtgac cgtgagctcc    360
ggaggcggcg gcagcggcgg cggaggcagc ggcggcggcg gcagcgacat cgtgatgaca    420
cagtccccta gcagcctgag cgctagcgtg ggcgacaggg tcacaatcac ctgcagggcc    480
agccaggatg tgaacaccgc cgtggcctgg taccaacaga agcccggcaa ggcccccaaa    540
ctgctgatct acagcgccag cttcctgtac tccggcgtgc cctccagatt cagcggcagc    600
aggagcggca ccgacttcac cctgaccatc agcagcctgc agcccgagga cttcgccacc    660
tactattgcc agcagcacta cacaaccccct cccaccttcg gccagggcac caaggtggag    720
atcaagagga ccgtggcttc catggttaga tctgacaaaa ctcacacatg cccaccgtgc    780
ccagcacctg aactcctggg gggaccgtca gtcttcctct tccccccaaa acccaaggac    840
accctcatga tctcccggac ccctgaggtc acatgcgtgg tggtggacgt gagccacgaa    900
gaccctgagg tcaagttcaa ctggtacgtg gacggcgtgg aggtgcataa tgccaagaca    960
aagccgcggg aggagcagta caacagcacg taccgtgtgg tcagcgtcct caccgtcctg    1020
caccaggact ggctgaatgg caaggagtac aagtgcaagg tctccaacaa agccctccca    1080
gcccccatcg agaaaaccat ctccaaagcc aaagggcagc cccgagaacc acaggtgtac    1140
accctgcccc catcccggga ggagatgacc aagaaccagg tcagcctgac ctgcctggtc    1200
aaaggcttct atcccagcga catcgccgtg gagtgggaga gcaatgggca gccggagaac    1260
aactacaaga ccgatgacga tgtgctggac tccgacggct ccttcttcct ctacagcaag    1320
ctcaccgtgg acaagagcag gtggcagcag gggaacgtct tctcatgctc cgtgatgcac    1380
gaggctctgc acaaccacta cacgcagaag agcctctccc tgtctccggg taaa          1434
```

<210> SEQ ID NO 3
<211> LENGTH: 476
<212> TYPE: PRT
<213> ORGANISM: Artificial sequence
<220> FEATURE:
<223> OTHER INFORMATION: Her2-OB2 heavy chain

<400> SEQUENCE: 3

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Gly Gly Gly Gly Ser Gly
            100                 105                 110

Gly Gly Gly Ser Gly Gly Gly Gly Ser Glu Val Gln Leu Val Glu Ser
        115                 120                 125

Gly Gly Gly Leu Val Gln Pro Gly Gly Ser Leu Arg Leu Ser Cys Ala
    130                 135                 140
```

Ala Ser Gly Phe Asn Ile Lys Asp Thr Tyr Ile His Trp Val Arg Gln
145                 150                 155                 160

Ala Pro Gly Lys Gly Leu Glu Trp Val Ala Arg Ile Tyr Pro Thr Asn
                165                 170                 175

Gly Tyr Thr Arg Tyr Ala Asp Ser Val Lys Gly Arg Phe Thr Ile Ser
            180                 185                 190

Ala Asp Thr Ser Lys Asn Thr Ala Tyr Leu Gln Met Asn Ser Leu Arg
        195                 200                 205

Ala Glu Asp Thr Ala Val Tyr Tyr Cys Ser Arg Trp Gly Gly Asp Gly
    210                 215                 220

Phe Tyr Ala Met Asp Tyr Trp Gly Gln Gly Thr Leu Val Thr Val Ser
225                 230                 235                 240

Ser Ala Ser Thr Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Asp Asp Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 4
<211> LENGTH: 1428
<212> TYPE: DNA
<213> ORGANISM: Artificial sequence
<220> FEATURE:
<223> OTHER INFORMATION: DNA sequence of Her2-OB2 heavy chain

<400> SEQUENCE: 4
gatatacaga tgacccagag cccaagttca ctgagcgcct ctgtcggcga tagagtgaca      60
atcacatgcc gcgcaagcca ggatgttaat accgcagtgg catggtatca acagaagccc     120
ggcaaggctc ccaaactgct gatctattct gccagcttcc tgtactccgg agtgccctcc     180

```
cgcttttccg gaagtcgctc tggaactgac ttcactctga ccatatcctc tctccagcca    240
gaggattttg ctacatacta ctgccagcag cattacacaa cacctccaac cttcggccag    300
ggcacaaagg tcgagattgg aggcggtgga agtggcggcg aggatcagg cggcggtggg     360 tctgaagtcc agctcgttga atctggtggc gggctcgtgc agcctggtgg ctcactgaga    420
ctctcctgtg ctgccagcgg attcaatatc aaggacacat atatccactg ggttcggcag    480
gctcctggga aagggctgga gtgggtggcc aggatctatc ctaccaacgg gtatacacgc    540
tacgccgata gcgtcaaagg gcggtttaca attagcgctg atactagcaa gaataccgcc    600
tacctccaga tgaatagtct ccgggcagaa gacaccgccg tttattactg tagtcgctgg    660
ggcggtgatg ggttttacgc aatggattac tggggtcagg gaaccctcgt gaccgtttca    720
tcagcatcca cagaacccaa gtcctgcgat aagacacaca cctgcccacc ctgccctgca    780
ccagagctgc tgggagggcc tagcgttttc ctgttccctc ccaaaccaaa ggacactctg    840
atgatctcca gaacacctga gtgacctgt gtggtggtgg atgttagcca cgaggaccca    900
gaagtcaagt ttaactggta cgtggacggt gtggaggtgc ataacgccaa aaccaaacct    960
cgggaagaac agtacaactc cacttatagg gtcgtctccg tgctcactgt tctccaccaa   1020
gattggctga acggtaagga atataagtgt aaagtgtcta ataaagctct gccagcacca   1080
attgagaaaa ccatttctaa agccaagggc cagccaaggg agccacaggt gtatacactg   1140
ccacctagca gggatgagct gaccaagaac caggtttcac tgacatgcct ggtgaagggc   1200
ttttatccaa gcgatattgc agtcgagtgg gaatccaacg gtcagcctga aacaactat    1260 aagaccgatg atgatgtgct cgatagtgac ggttcattct cctctacag caaactgacc    1320 gttgacaaga gtcgctggca gcagggaaat gtttttcagtt gctcagtgat gcatgaagca   1380
ctccataacc actatacaca gaaatccctg tccctgtctc ccggaaaa                 1428
```

<210> SEQ ID NO 5
<211> LENGTH: 476
<212> TYPE: PRT
<213> ORGANISM: Artificial sequence
<220> FEATURE:
<223> OTHER INFORMATION: Her2-OB3 heavy chain

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140
```

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
210                 215                 220

Gln His Tyr Thr Thr Pro Pro Thr Phe Gly Gln Gly Thr Lys Val Glu
225                 230                 235                 240

Ile Lys Arg Gly Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Asp Asp Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
450                 455                 460

Tyr Thr Gln Lys Ser Leu Ser Leu Ser Pro Gly Lys
465                 470                 475

<210> SEQ ID NO 6
<211> LENGTH: 1428
<212> TYPE: DNA
<213> ORGANISM: Artificial sequence
<220> FEATURE:
<223> OTHER INFORMATION: DNA sequence of Her2-OB3 heavy chain

<400> SEQUENCE: 6
gaagtccagc tcgttgaatc tggtggcggg ctcgtgcagc ctggtggctc actgagactc        60
tcctgtgctg ccagcggatt caatatcaag gacacatata tccactgggt tcggcaggct       120
cctgggaaag ggctggagtg ggtggccagg atctatccta ccaacgggta tacacgctac       180

```
gccgatagcg tcaaagggcg gtttacaatt agcgctgata ctagcaagaa taccgcctac    240
ctccagatga atagtctccg ggcagaagac accgccgttt attactgtag tcgctggggc    300
ggtgatgggt tttacgcaat ggattactgg ggtcagggaa ccctcgtgac cgtttcatca    360
ggaggcggtg aagtggcgg cggaggatca ggcggcggtg gtctgatat acagatgacc     420 cagagcccaa gttcactgag cgcctctgtc ggcgatagag tgacaatcac atgccgcgca    480
agccaggatg ttaataccgc agtggcatgg tatcaacaga gcccggcaa ggctcccaaa    540 ctgctgatct attctgccag cttcctgtac tccggagtgc cctcccgctt tccggaagt     600 cgctctggaa ctgacttcac tctgaccata tcctctctcc agccagagga ttttgctaca    660
tactactgcc agcagcatta cacaacacct ccaaccttcg gccagggcac aaaggtcgag    720
attaaaagag cgaacccaa gtcctgcgat aagacacaca cctgcccacc ctgccctgca     780
ccagagctgc tgggagggcc tagcgttttc ctgttccctc ccaaaccaaa ggacactctg    840
atgatctcca gaacacctga agtgacctgt gtggtggtgg atgttagcca cgaggaccca    900
gaagtcaagt ttaactggta cgtggacggt gtggaggtgc ataacgccaa aaccaaacct    960
cgggaagaac agtacaactc cacttatagg gtcgtctccg tgctcactgt ctccaccaa    1020 gattggctga acggtaagga atataagtgt aaagtgtcta ataaagctct gccagcacca   1080
attgagaaaa ccatttctaa agccaagggc agccaaggg agccacaggt gtatacactg    1140
ccacctagca gggatgagct gaccaagaac caggtttcac tgacatgcct ggtgaagggc   1200
ttttatccaa gcgatattgc agtcgagtgg gaatccaacg gtcagcctga aacaactat    1260 aagaccgatg atgatgtgct cgatagtgac ggttcattct tcctctacag caaactgacc   1320
gttgacaaga gtcgctggca gcagggaaat gttttcagtt gctcagtgat gcatgaagca   1380
ctccataacc actatacaca gaaatccctg tccctgtctc ccggaaaa               1428
```

<210> SEQ ID NO 7
<211> LENGTH: 476
<212> TYPE: PRT
<213> ORGANISM: Artificial sequence
<220> FEATURE:
<223> OTHER INFORMATION: Her2-OB4 heavy chain

<400> SEQUENCE: 7

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140
```

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
            165                 170                 175

Lys Ala Pro Lys Leu Leu Ile Tyr Ser Ala Ser Phe Leu Tyr Ser Gly
        180                 185                 190

Val Pro Ser Arg Phe Ser Gly Ser Arg Ser Gly Thr Asp Phe Thr Leu
    195                 200                 205

Thr Ile Ser Ser Leu Gln Pro Glu Asp Phe Ala Thr Tyr Tyr Cys Gln
210                 215                 220

Gln His Tyr Thr Thr Pro Pro Thr Phe Gly Gln Gly Thr Lys Val Glu
225                 230                 235                 240

Ile Lys Arg Gly Glu Pro Lys Ser Cys Asp Lys Thr His Thr Cys Pro
                245                 250                 255

Pro Cys Pro Ala Pro Glu Ala Ala Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Asp Asp Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 8
<211> LENGTH: 1428
<212> TYPE: DNA
<213> ORGANISM: Artificial sequence
<220> FEATURE:
<223> OTHER INFORMATION: DNA sequence of Her2-OB4 heavy chain

<400> SEQUENCE: 8
gaagtccagc tcgttgaatc tggtggcggg ctcgtgcagc ctggtggctc actgagactc        60
tcctgtgctg ccagcggatt caatatcaag gacacatata tccactgggt tcggcaggct       120
cctgggaaag ggctggagtg ggtggccagg atctatccta ccaacgggta tacacgctac       180

```
gccgatagcg tcaaagggcg gtttacaatt agcgctgata ctagcaagaa taccgcctac    240
ctccagatga atagtctccg ggcagaagac accgccgttt attactgtag tcgctggggc    300
ggtgatgggt tttacgcaat ggattactgg ggtcaggaa ccctcgtgac cgtttcatca    360
ggaggcggtg aagtggcgg cggaggatca ggcggcggtg gtctgatat acagatgacc    420 cagagcccaa gttcactgag cgcctctgtc ggcgatagag tgacaatcac atgccgcgca    480
agccaggatg ttaataccgc agtggcatgg tatcaacaga agcccggcaa ggctcccaaa    540
ctgctgatct attctgccag cttcctgtac tccggagtgc cctcccgctt tccggaagt    600 cgctctggaa ctgacttcac tctgaccata tcctctctcc agccagagga ttttgctaca    660
tactactgcc agcagcatta cacaacacct ccaaccttcg gccagggcac aaaggtcgag    720
attaaaagag cgaacccaa gtcctgcgat aagacacaca cctgcccacc ctgccctgca    780
ccagaggctg caggagggcc tagcgttttc ctgttccctc ccaaaccaaa ggacactctg    840
atgatctcca gaacacctga gtgaccgtt gtggtggtgg atgttagcca cgaggaccca    900
gaagtcaagt ttaactggta cgtggacggt gtggaggtgc ataacgccaa aaccaaacct    960
cgggaagaac agtacaactc cacttatagg gtcgtctccg tgctcactgt tctccaccaa   1020
gattggctga acggtaagga atataagtgt aaagtgtcta ataaagctct gccagcacca   1080
attgagaaaa ccatttctaa agccaagggc agccaaggg agccacaggt gtatacactg   1140
ccacctagca gggatgagct gaccaagaac caggtttcac tgacatgcct ggtgaagggc   1200
ttttatccaa gcgatattgc agtcgagtgg gaatccaacg gtcagcctga aacaactat   1260 aagaccgatg atgatgtgct cgatagtgac ggttcattct tcctctacag caaactgacc   1320
gttgacaaga gtcgctggca gcagggaaat gttttcagtt gctcagtgat gcatgaagca   1380
ctccataacc actatacaca gaaatccctg tccctgtctc ccggaaaa               1428
```

<210> SEQ ID NO 9
<211> LENGTH: 455
<212> TYPE: PRT
<213> ORGANISM: Artificial sequence
<220> FEATURE:
<223> OTHER INFORMATION: GXP2 heavy chain

<400> SEQUENCE: 9

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140
```

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
        180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Lys Lys Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 10
<211> LENGTH: 1368
<212> TYPE: DNA
<213> ORGANISM: Artificial sequence
<220> FEATURE:
<223> OTHER INFORMATION: DNA sequence of GXP2 heavy chain

<400> SEQUENCE: 10
gaagtgcaac tggttgaaag cggtggagga ctggttcagc ctggaggctc cctcaaactc      60
agttgcgccg cttccggttt tacattcaac acttatgcca tgaattgggt gcgccaggct     120
cccggaaaag gcctggaatg ggtggcacgg atcaggagca aatacaacaa ttacgccaca     180
tattacgctg actccgttaa agacagattc acaatttcca gagatgattc caagaatact     240

```
gcttatctcc agatgaacaa cctgaagaca gaggatacag ctatgtacta ttgcgtgcgg    300
catggcaatt tcggaaattc ctatgtgagt tggtttgcct actggggaca gggaactctc    360
gttactgtca gctccgccag taccaagggc ccatccgttt tccctctggc accctcctcc    420
aaatcaacaa gcggcgggac tgccgccctc gggtgtctgg tgaaagacta cttcccagaa    480
cccgtcaccg tgagttggaa cagtggcgcc ctcacctctg gagtccatac ctttccagcc    540
gtcctgcagt ccagcggact gtattccctc tccagtgtgg tgaccgtgcc tagcagctct    600
ctgggcacac aaacatacat ctgtaacgtt aaccataagc ccagcaacac aaaagtggat    660
aagaaggtgg agccaaagag ttgcgacaag actcacactt gtccaccttg cccagcaccc    720
gaagctgccg gcggtccaag cgtgtttctc tttcctccaa agcccaagga caccctgatg    780
atctctcgca ctcctgaggt gacctgtgtg gtcgttgacg tgtcacacga agacccagag    840
gttaagttta attggtatgt ggatggcgtg gaggttcaca acgctaaaac taagccaaga    900
gaggagcagt ataactcaac ataccgggtc gtgagcgtgc tgaccgtgct gcaccaagac    960
tggctcaatg gcaaggaata caagtgcaaa gtgagcaata aggccctgcc agcacctatt   1020
gagaagacaa tcagtaaagc caagggtcag cctcgcgagc tcaggtgta caccctgcct   1080 ccttcacggg acgaactcac aaagaatcag gtgagcctga cctgcctcgt caagggattt   1140
tatccctccg acatcgcagt tgaatgggag agcaatggtc agcccgagaa caattacaaa   1200
accactaaga gaagctgga ttcagatggc agtttctttc tgtacagtaa actcaccgtt   1260
gacaagagtc ggtggcagca gggtaacgtg ttctcctgta gtgtcatgca cgaagcactg   1320
cataatcact acactcagaa gtctctcagt ctgtctcctg gaaagtga                1368
```

<210> SEQ ID NO 11
<211> LENGTH: 216
<212> TYPE: PRT
<213> ORGANISM: Artificial sequence
<220> FEATURE:
<223> OTHER INFORMATION: GXP2 light chain

<400> SEQUENCE: 11

```
Asp Ile Gln Met Thr Gln Glu Pro Ser Leu Thr Thr Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Ile Gly Gly Lys Ala Ala Leu Thr Ile Thr Gly Val
65                  70                  75                  80

Gln Pro Glu Asp Glu Ala Ile Tyr Phe Cys Ala Leu Trp Tyr Ser Asn
                85                  90                  95

Leu Trp Val Phe Gly Gly Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
```

```
              165                 170                 175
Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 12
<211> LENGTH: 648
<212> TYPE: DNA
<213> ORGANISM: Artificial sequence
<220> FEATURE:
<223> OTHER INFORMATION: DNA sequence of  GXP2 light chain

<400> SEQUENCE: 12
gatattcaga tgacacaaga accaagtctc actacaagcc ctggaggcac cgttacactg      60
acctgtcgct cttccactgg cgccgtgacc acttccaact atgcaaactg ggtgcaggag     120
aaacctggac aggctcctag aggtctgatt ggaggcacta caagagagc tccagggact      180 cctgccaggt tcagcggatc tctgatcggt gggaaggcag ctctgacaat cactggagtg     240
caacccgagg atgaggctat ctacttctgt gctctctggt actcaaatct gtgggtgttc     300
ggaggtggaa caaagctgga gatcaagcgg actgtcgcag ctccatccgt gttcatcttt     360
ccaccctccg acgagcaact gaaaagtggc acagcctccg tcgtctgtct gctgaacaat     420
ttctaccctc gggaggccaa ggtccagtgg aaggtggaca cgctctccca gagtggaaat     480
agccaagagt ccgttactga gcaggactct aaggattcaa cctacagcct ctccagcacc     540
ctgactctga gcaaggcaga ttatgagaag cacaaagtct acgcatgtga agtgactcat     600
cagggactca gctcacccgt taccaagtct ttcaacaggg gagagtgt                  648

<210> SEQ ID NO 13
<211> LENGTH: 440
<212> TYPE: PRT
<213> ORGANISM: Artificial sequence
<220> FEATURE:
<223> OTHER INFORMATION: GXP heavy chain

<400> SEQUENCE: 13

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ile Ser Ser
        115                 120                 125

Ala Ser Thr Lys Gly Pro Ser Val Phe Pro Leu Ala Pro Ser Ser Lys
    130                 135                 140
```

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
            165                 170                 175

Gly Val His Thr Phe Pro Ala Val Leu Gln Ser Ser Gly Leu Tyr Ser
        180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Gln Glu Glu Ala Gly Leu Arg Arg Leu Leu Leu
                405                 410                 415

Pro Leu Gln Gln Ala His Arg Gly Gln Glu Gln Val Ala Ala Gly Glu
            420                 425                 430

Arg Leu Leu Met Leu Arg Asp Ala
        435                 440

<210> SEQ ID NO 14
<211> LENGTH: 1323
<212> TYPE: DNA
<213> ORGANISM: Artificial sequence
<220> FEATURE:
<223> OTHER INFORMATION: DNA sequence of GXP heavy chain

<400> SEQUENCE: 14
gaggtgaagc tgctggaaag cggcggagga ctggtgcagc caaagggatc actgaaactg      60
tcctgcgccg cctccggctt cacctttaac acatacgcta tgaattgggt gcgacaggca     120
cctggcaagg gcctggagtg ggtggcaagg atcaggtcca agtacaacaa ttatgcaacc     180
tactatgccg actctgtgaa ggatagattc acaatcagtc gcgacgattc cagagcatt     240 ctgtatctgc agatgaacaa tctgaaaact gaagacaccg ccatgtacta ttgtgtgcgg     300
cacggtaact tcggcaattc ttacgtgtct tggtttgctt attgggaca ggggacactg      360

```
gtgactgtgt cttccatctc gagtgctagc accaagggcc catcggtctt ccccctggca     420 cccctcctcca agagcacctc tgggggcaca gcggccctgg gctgcctggt caaggactac     480
ttccccgaac cggtgacggt gtcgtggaac tcaggcgccc tgaccagcgg cgtgcacacc     540
ttcccggctg tcctacagtc ctcaggactc tactccctca gcagcgtggt gaccgtgccc     600
tccagcagct tgggcaccca gacctacatc tgcaacgtga atcacaagcc cagcaacacc     660
aaggtggaca gaaagttga gcccaaatct tgtgacaaaa ctcacacatg cccaccgtgc     720
ccagcacctg aactcctggg gggaccgtca gtcttcctct tccccccaaa acccaaggac     780
accctcatga tctcccggac ccctgaggtc acatgcgtgg tggtggacgt gagccacgaa     840
gaccctgagg tcaagttcaa ctggtacgtg gacggcgtgg aggtgcataa tgccaagaca     900
aagccgcggg aggagcagta caacagcacg taccgtgtgg tcagcgtcct caccgtcctg     960
caccaggact ggctgaatgg caaggagtac aagtgcaagg tctccaacaa agccctccca    1020
gcccccatcg agaaaaccat ctccaaagcc aaagggcagc cccgagaacc acaggtgtac    1080
accctgcccc catcccggga ggagatgacc aagaaccagg tcagcctgac ctgcctggtc    1140
aaaggcttct atcccagcga catcgccgtg gagtgggaga gcaatgggca gccggagaac    1200
aactacaaga ccacgcaaga gaagctgga ctccgacggc tccttcttcc tctacagcaa    1260
gctcaccgtg gacaagagca ggtggcagca ggggaacgtc ttctcatgct ccgtgatgca    1320
tga                                                                 1323
```

<210> SEQ ID NO 15
<211> LENGTH: 219
<212> TYPE: PRT
<213> ORGANISM: Artificial sequence
<220> FEATURE:
<223> OTHER INFORMATION: GXP light chain

<400> SEQUENCE: 15

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Val Thr Met Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
```

```
                    180                 185                 190
Lys His Lys Val Tyr Thr Cys Glu Val Thr His Gln Gly Leu Ser Ser
            195                 200                 205

Pro Val Thr Lys Ser Phe Asn Arg Gly Glu Cys
        210                 215

<210> SEQ ID NO 16
<211> LENGTH: 660
<212> TYPE: DNA
<213> ORGANISM: Artificial sequence
<220> FEATURE:
<223> OTHER INFORMATION: DNA sequence of GXP light chain

<400> SEQUENCE: 16
caggccgtgg tgacacagga gtcagctctg accacatccc caggcgaaac agtgactctg      60
acctgcagat ccagcactgg agcagtgact acctctaact acgctaattg ggtgcaggag     120
aagcccgacc acctgttcac tgggctgatc ggcggaacca acaaaagggc acccggtgtg     180
cctgcccggt tttctggcag tctgatcgga gacaaggccg ctctgacaat tactggcgcc     240
cagacagagg atgaagctat ttacttctgt gcactgtggt atagcaatct gtgggtgttt     300
gggggtggca ccaagcttgt caccatggaa atcaaacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cacctgcgaa     600
gtcacccatc agggcctgag ctcgcccgtc acaaagagct tcaacagggg agagtgttag     660

<210> SEQ ID NO 17
<211> LENGTH: 437
<212> TYPE: PRT
<213> ORGANISM: Artificial sequence
<220> FEATURE:
<223> OTHER INFORMATION: C31 heavy chain

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160
```

```
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Gln Thr Tyr Ile Cys
        195                 200                 205
Asn Val Asn His Lys Pro Ser Asn Thr Lys Val Asp Lys Lys Val Glu
    210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
    290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Glu Glu Met Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Lys Lys Lys Leu Asp Ser Asp Gly Ser Phe Phe Leu Tyr Ser
                405                 410                 415
Lys Leu Thr Val Gly Gln Glu Gln Val Ala Ala Gly Glu Arg Leu Leu
            420                 425                 430
Met Leu Arg Asp Ala
        435

<210> SEQ ID NO 18
<211> LENGTH: 1314
<212> TYPE: DNA
<213> ORGANISM: Artificial sequence
<220> FEATURE:
<223> OTHER INFORMATION: DNA sequence of C31 heavy chain

<400> SEQUENCE: 18
gaggtgcagc tggtggaaag cggggggtgga ctggtgcagc ctggtggtag cctgcgactg      60
tcttgtgccg cttctggttt cactttcaac acatacgcca tgaattgggt gagacaggct     120
ccaggcaagg gactggagtg gtggctcgg atcaggtcta agtacaacaa ttatgccaca     180
tactatgctg acagcgtgaa ggatagattc accatctccc gcgacgatag caagaactcc     240
ctgtatctgc agatgaatag cctgaagaca gaggacaccg ccgtgtacta ttgcgctcgc     300
cacggcaact cggcaattc ttacgtgagc tggtttgcct attggggcca gggcacactg     360
gtgactgtgt cttccgctag caccaagggc ccatcggtct tccccctggc accctcctcc     420
```

```
aagagcacct ctgggggcac agcggccctg ggctgcctgg tcaaggacta cttccccgaa    480
ccggtgacgg tgtcgtggaa ctcaggcgcc ctgaccagcg gcgtgcacac cttcccggct    540
gtcctacagt cctcaggact ctactccctc agcagcgtgg tgaccgtgcc ctccagcagc    600
ttgggcaccc agacctacat ctgcaacgtg aatcacaagc ccagcaacac caaggtggac    660
aagaaagttg agcccaaatc ttgtgacaaa actcacacat gcccaccgtg cccagcacct    720
gaactcctgg ggggaccgtc agtcttcctc ttccccccaa aacccaagga caccctcatg    780
atctcccgga cccctgaggt cacatgcgtg gtggtggacg tgagccacga agaccctgag    840
gtcaagttca actggtacgt ggacggcgtg gaggtgcata atgccaagac aaagccgcgg    900
gaggagcagt acaacagcac gtaccgtgtg gtcagcgtcc tcaccgtcct gcaccaggac    960
tggctgaatg gcaaggagta caagtgcaag gtctccaaca aagccctccc agcccccatc   1020
gagaaaacca tctccaaagc caaagggcag ccccgagaac acaggtgta cacc ctgccc   1080
ccatcccggg aggagatgac caagaaccag gtcagcctga cctgcctggt caaaggcttc   1140
tatcccagcg acatcgccgt ggagtgggag agcaatgggc agccggagaa caactacaag   1200
accacgaaga gaagctgga ctccgacggc tccttcttcc tctacagcaa gctcaccgtg    1260
ggacaagagc aggtggcagc aggggaacgt cttctcatgc tccgtgatgc atga          1314
```

<210> SEQ ID NO 19
<211> LENGTH: 217
<212> TYPE: PRT
<213> ORGANISM: Artificial sequence
<220> FEATURE:
<223> OTHER INFORMATION: C31 light chain

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Leu Val Thr Met Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Thr Cys Glu Val Thr His Gln Gly Leu Ser Ser Pro Val
        195                 200                 205
```

```
Thr Lys Ser Phe Asn Arg Gly Glu Cys
    210                 215
```

<210> SEQ ID NO 20
<211> LENGTH: 654
<212> TYPE: DNA
<213> ORGANISM: Artificial sequence
<220> FEATURE:
<223> OTHER INFORMATION: DNA sequence of C31 light chain

<400> SEQUENCE: 20

```
gacatccaga tgacccagag cccttcctcc ctgtccgcca gcgtgggaga cagggtgaca    60
atcacctgca gggcctccca ggatatccgg aactacctga ctggtacca gcagaagccc   120 ggcaaggccc ccaagctgct gatctactac accagcaggc tggagtccgg agtgccctcc   180
aggttttccg gctccggcag cggaaccgac tacaccctga ccatctccag cctgcagccc   240
gaggacttcg ccacctacta ctgtcagcag ggcaacacac tgccttggac ctttggccag   300
ggcaccaagc ttgtcaccat ggaaatcaaa cgtacggtgg ctgcaccatc tgtcttcatc   360
ttcccgccat ctgatgagca gttgaaatct ggaactgcct ctgttgtgtg cctgctgaat   420
aacttctatc ccagagaggc caaagtacag tggaaggtgg ataacgccct ccaatcgggt   480
aactcccagg agagtgtcac agagcaggac agcaaggaca gcacctacag cctcagcagc   540
accctgacgc tgagcaaagc agactacgag aaacacaaag tctacacctg cgaagtcacc   600
catcagggcc tgagctcgcc cgtcacaaag agcttcaaca ggggagagtg ttag          654
```

<210> SEQ ID NO 21
<211> LENGTH: 125
<212> TYPE: PRT
<213> ORGANISM: Artificial sequence
<220> FEATURE:
<223> OTHER INFORMATION: GXP2 heavy chain VH

<400> SEQUENCE: 21

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 22
<211> LENGTH: 109
<212> TYPE: PRT
<213> ORGANISM: Artificial sequence
<220> FEATURE:
<223> OTHER INFORMATION: GXP2 light chain VL

<400> SEQUENCE: 22

-continued

```
Asp Ile Gln Met Thr Gln Glu Pro Ser Leu Thr Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Ile Gly Gly Lys Ala Ala Leu Thr Ile Thr Gly Val
65                  70                  75                  80

Gln Pro Glu Asp Glu Ala Ile Tyr Phe Cys Ala Leu Trp Tyr Ser Asn
                85                  90                  95

Leu Trp Val Phe Gly Gly Gly Thr Lys Leu Glu Ile Lys
            100                 105
```

<210> SEQ ID NO 23
<211> LENGTH: 15
<212> TYPE: PRT
<213> ORGANISM: Artificial Sequence
<220> FEATURE:
<223> OTHER INFORMATION: connecting peptide

<400> SEQUENCE: 23

```
Gly Gly Gly Gly Ser Gly Gly Gly Gly Ser Gly Gly Gly Gly Ser
1               5                   10                  15
```

<210> SEQ ID NO 24
<211> LENGTH: 6
<212> TYPE: PRT
<213> ORGANISM: Artificial Sequence
<220> FEATURE:
<223> OTHER INFORMATION: non-human sequence element due to NcoI and Bgl
      II multiple cloning sites

<400> SEQUENCE: 24

```
Thr Val Ala Met Val Arg
1               5
```

<210> SEQ ID NO 25
<211> LENGTH: 4
<212> TYPE: PRT
<213> ORGANISM: Artificial Sequence
<220> FEATURE:
<223> OTHER INFORMATION: human replacement sequence for SEQ ID NO 24

<400> SEQUENCE: 25

```
Gly Glu Pro Lys
1
```

<210> SEQ ID NO 26
<211> LENGTH: 125
<212> TYPE: PRT
<213> ORGANISM: Artificial Sequence
<220> FEATURE:
<223> OTHER INFORMATION: C31 heavy chain VH

<400> SEQUENCE: 26

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Tyr Arg Gln Ala Pro Gly Lys Gly Leu Glu Trp Val
        35                  40                  45
```

```
Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 27
<211> LENGTH: 125
<212> TYPE: PRT
<213> ORGANISM: Artificial Sequence
<220> FEATURE:
<223> OTHER INFORMATION: GXP heavy chain VH

<400> SEQUENCE: 27

```
Glu Val Lys Leu Leu Glu Ser Gly Gly Gly Leu Val Gln Pro Lys Gly
 1               5                  10                  15

Ser Leu Lys Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
                35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Gln Ser Ile
 65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 28
<211> LENGTH: 110
<212> TYPE: PRT
<213> ORGANISM: Artificial Sequence
<220> FEATURE:
<223> OTHER INFORMATION: C31 light chain VL

<400> SEQUENCE: 28

```
Gln Ala Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Pro Arg Gly
                35                  40                  45

Leu Ile Gly Gly Thr Asn Lys Arg Ala Pro Trp Thr Pro Ala Arg Phe
        50                  55                  60

Ser Gly Ser Leu Leu Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly
```

<210> SEQ ID NO 29
<211> LENGTH: 109
<212> TYPE: PRT
<213> ORGANISM: Artificial Sequence
<220> FEATURE:
<223> OTHER INFORMATION: GXP light chain VL

<400> SEQUENCE: 29

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 30
<211> LENGTH: 106
<212> TYPE: PRT
<213> ORGANISM: Artificial Sequence
<220> FEATURE:
<223> OTHER INFORMATION: GXP2 light chain VL Table 1B

<400> SEQUENCE: 30

```
Asp Ile Gln Met Thr Gln Glu Pro Ser Leu Thr Thr Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Ile Gly Gly Lys Ala Ala Leu Thr Ile Thr Gly Val
65                  70                  75                  80

Gln Pro Glu Asp Glu Ala Ile Tyr Phe Cys Ala Leu Trp Tyr Ser Asn
                85                  90                  95

Leu Trp Val Phe Gly Gly Gly Thr Lys Leu
            100                 105
```

<210> SEQ ID NO 31
<211> LENGTH: 20
<212> TYPE: PRT
<213> ORGANISM: Artificial Sequence
<220> FEATURE:
<223> OTHER INFORMATION: connecting peptide

<400> SEQUENCE: 31

```
Gly Gly Gly Gly Ser Gly Gly Gly Gly Ser Gly Gly Gly Gly Ser Gly
1               5                   10                  15

Gly Gly Gly Ser
            20
```

```
<210> SEQ ID NO 32
<211> LENGTH: 25
<212> TYPE: PRT
<213> ORGANISM: Artificial Sequence
<220> FEATURE:
<223> OTHER INFORMATION: connecting peptide

<400> SEQUENCE: 32

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```